United States Patent
Song

(10) Patent No.: US 9,273,292 B2
(45) Date of Patent: *Mar. 1, 2016

(54) CHINESE HAMSTER OVARY CELL LINES

(71) Applicant: **AGENCY FOR SCIENCE, TECHNOLOGY AND RESEARCH (A*STAR)**, Singapore (SG)

(72) Inventor: Zhiwei Song, Singapore (SG)

(73) Assignee: **AGENCY FOR SCIENCE, TECHNOLOGY AND RESEARCH (A*STAR)**, Singapore (SG)

(*) Notice: Subject to any disclaimer, the term of this patent is extended or adjusted under 35 U.S.C. 154(b) by 0 days.

This patent is subject to a terminal disclaimer.

(21) Appl. No.: 14/636,795

(22) Filed: Mar. 3, 2015

(65) Prior Publication Data

US 2015/0184135 A1 Jul. 2, 2015

Related U.S. Application Data

(62) Division of application No. 13/119,461, filed as application No. PCT/SG2009/000348 on Sep. 18, 2009, now Pat. No. 9,012,176.

(60) Provisional application No. 61/098,270, filed on Sep. 19, 2008, provisional application No. 61/183,647, filed on Jun. 3, 2009.

(51) Int. Cl.
*C12N 15/00* (2006.01)
*C12P 21/00* (2006.01)
*C12N 9/10* (2006.01)
*C07K 14/505* (2006.01)
*C07K 14/57* (2006.01)

(52) U.S. Cl.
CPC ............ *C12N 9/1051* (2013.01); *C07K 14/505* (2013.01); *C07K 14/57* (2013.01); *C12P 21/005* (2013.01); *C12Y 204/0115* (2013.01); *C12N 2510/02* (2013.01)

(58) Field of Classification Search
CPC ..... A61K 38/00; A61K 38/446; C12N 9/0089
USPC ........................................................ 435/252.3
See application file for complete search history.

(56) References Cited

U.S. PATENT DOCUMENTS

2005/0181359 A1 8/2005 Optelten et al.

OTHER PUBLICATIONS

Chen et al. Glycobiology 13(1):43-50 (2003). "Five lec1 CHO cell mutants have distinct Mgat1 gene mutations that encode truncated N-acetylglucosaminyltransferase I.".
Cummings et al., Biochemical and Biophysical Research Communication 195(2):814-822 (1993). "Antisense and sense cDNA expression cloning using autonomously replicating vectors and toxic lectin selection.".
Gottlier et al., Journal of Biological Chemistry 250(9):3303-3309 (1975). "Deficient uridine diphosphate-N-acetylglucosamine:Glycoprotein N-acetylglucosaminyltransferase activity in a clone of Chinese hamster ovary cells with altered surfaced glycoproteins.".
Hong et al., Biochemical and Biophysical Research Communications 335:1060-1069 (2003). "New mutants Chinese hamster ovary cell representing an unknown gene for attachment of glycosylphosphatidylinositol to proteins.".
Puthalakath et al., Journal of Biological Chemistry 271(44):27818-27822 (1996). "Glycosylation defect in Led Chinese hamster ovary mutant is due to a point mutation in N-Acetylglucosaminyltransferase I gene."
Ripka et al., Biochemical and Biophysical Research Communications 159(2):554-560 (1989). "DNA-Mediated transformation of N-acetylglucosaminyltransferase I activity into an enzyme deficient cell line."
Ripka et al., Journal of Cellular Biochemistry 42:117-122 (1990). "Co-transforamtion of Lec1 CHO cells with N-acetylgucosaminyltransferace 1 activity and a selectable marker."

*Primary Examiner* — Maryam Monshipouri
(74) *Attorney, Agent, or Firm* — Nixon Peabody LLP; Mark J. FitzGerald

(57) ABSTRACT

We provide a Chinese Hamster Ovary (CHO) cell which is capable of higher protein sialylation compared to a wild type Chinese Hamster Ovary cell, such as in the presence of functional GnT 1, in which the CHO cell is obtainable by selection with *Ricinus communis* agglutinin I (RCA-I).

12 Claims, 12 Drawing Sheets

SEQUENCE LISTING

<160> NUMBER OF SEQ ID NOS: 2

<210> SEQ ID NO 1
<211> LENGTH: 1344

```
<212> TYPE: DNA
<213> ORGANISM: Cricetulus griseus

<400> SEQUENCE: 1
atgctgaaga agcagtctgc agggcttgtg ctttggggtg ctatcctctt tgtgggctgg      60
aatgccctgc tgctcctctt cttctggaca cgcccagccc ctggcaggcc cccctcagat     120
agtgctatcg atgatgaccc tgccagcctc acccgtgagg tgttccgcct ggctgaggac     180
gctgaggtgg agttggagcg gcagcggggg ctgttgcagc aaatcaggga gcatcatgct     240
ttgtggagac agaggtggaa agtgcccacc gtggcccctc agcctggcc ccgtgtgcct      300
gcgaccccct caccagccgt gatccccatc ctggtcattg cctgtgaccg cagcactgtc     360
cggcgctgct tggataagtt gttgcactat cggccctcag ctgagcattt ccccatcatt     420
gtcagccagg actgcgggca cgaagagaca gcacaggtca ttgcttccta tggcagtgca     480
gtcacacaca tccggcagcc agacctgagt aacatcgctg tgcccccaga ccaccgcaag     540
ttccagggtt actacaagat cgccaggcac taccgctggg cactgggcca gatcttcaac     600
aagttcaagt tcccagcagc tgtggtagtg gaggacgatc tggaggtggc accagacttc     660
tttgagtact tccaggccac ctacccactg ctgagaacag acccctccct ttggtgtgtg     720
tctgcttgga atgacaatgg caaggagcag atggtagact caagcaaacc tgagctgctc     780
tatcgaacag actttttttcc tggccttggc tggctgctga tggctgagct gtggacagag     840
ctggagccca agtggcccaa ggccttctgg gatgactgga tgcgcagacc tgagcagcgg     900
aaggggcggg cctgtattcg tccagaaatt tcaagaacga tgacctttgg ccgtaagggt     960
gtgagccatg ggcagttctt tgatcagcat cttaagttca tcaagctgaa ccagtagttc    1020
gtgtctttca cccagttgga tttgtcatac ttgcagcggg aggcttatga ccgggatttc    1080
cttgcccgtg tctatagtgc ccccctgcta caggtggaga agtgaggac caatgatcag    1140
aaggagctgg gggaggtgcg ggtacagtac actagcagag acagcttcaa ggcctttgct    1200
aaggccctgg gtgtcatgga tgacctcaag tctggtgtcc ccagagctgg ctaccggggc    1260
gttgtcactt tccagttcag gggtcgacgt gtccacctgg caccccaca aacctgggaa    1320
ggctatgatc ctagctggaa ttag                                           1344

<210> SEQ ID NO 2
<211> LENGTH: 447
<212> TYPE: PRT
<213> ORGANISM: Cricetulus griseus

<400> SEQUENCE: 2

Met Leu Lys Lys Gln Ser Ala Gly Leu Val Leu Trp Gly Ala Ile Leu
1               5                   10                  15

Phe Val Gly Trp Asn Ala Leu Leu Leu Leu Phe Phe Trp Thr Arg Pro
                20                  25                  30

Ala Pro Gly Arg Pro Pro Ser Asp Ser Ala Ile Asp Asp Asp Pro Ala
            35                  40                  45

Ser Leu Thr Arg Glu Val Phe Arg Leu Ala Glu Asp Ala Glu Val Glu
        50                  55                  60

Leu Glu Arg Gln Arg Gly Leu Leu Gln Gln Ile Arg Glu His His Ala
65                  70                  75                  80

Leu Trp Arg Gln Arg Trp Lys Val Pro Thr Val Ala Pro Ala Pro Ala Trp
                85                  90                  95

Pro Arg Val Pro Ala Thr Pro Ser Pro Ala Val Ile Pro Ile Leu Val
            100                 105                 110
```

```
Ile Ala Cys Asp Arg Ser Thr Val Arg Arg Cys Leu Asp Lys Leu Leu
    115                 120                 125

His Tyr Arg Pro Ser Ala Glu His Phe Pro Ile Ile Val Ser Gln Asp
    130                 135                 140

Cys Gly His Glu Glu Thr Ala Gln Val Ile Ala Ser Tyr Gly Ser Ala
145                 150                 155                 160

Val Thr His Ile Arg Gln Pro Asp Leu Ser Asn Ile Ala Val Pro Pro
                165                 170                 175

Asp His Arg Lys Phe Gln Gly Tyr Tyr Lys Ile Ala Arg His Tyr Arg
                180                 185                 190

Trp Ala Leu Gly Gln Ile Phe Asn Lys Phe Lys Phe Pro Ala Ala Val
            195                 200                 205

Val Val Glu Asp Asp Leu Glu Val Ala Pro Asp Phe Phe Glu Tyr Phe
        210                 215                 220

Gln Ala Thr Tyr Pro Leu Leu Arg Thr Asp Pro Ser Leu Trp Cys Val
225                 230                 235                 240

Ser Ala Trp Asn Asp Asn Gly Lys Glu Gln Met Val Asp Ser Ser Lys
                245                 250                 255

Pro Glu Leu Leu Tyr Arg Thr Asp Phe Phe Pro Gly Leu Gly Trp Leu
                260                 265                 270

Leu Met Ala Glu Leu Trp Thr Glu Leu Glu Pro Lys Trp Pro Lys Ala
        275                 280                 285

Phe Trp Asp Asp Trp Met Arg Arg Pro Glu Gln Arg Lys Gly Arg Ala
        290                 295                 300

Cys Ile Arg Pro Glu Ile Ser Arg Thr Met Thr Phe Gly Arg Lys Gly
305                 310                 315                 320

Val Ser His Gly Gln Phe Phe Asp Gln His Leu Lys Phe Ile Lys Leu
                325                 330                 335

Asn Gln Gln Phe Val Ser Phe Thr Gln Leu Asp Leu Ser Tyr Leu Gln
            340                 345                 350

Arg Glu Ala Tyr Asp Arg Asp Phe Leu Ala Arg Val Tyr Ser Ala Pro
        355                 360                 365

Leu Leu Gln Val Glu Lys Val Arg Thr Asn Asp Gln Lys Glu Leu Gly
    370                 375                 380

Glu Val Arg Val Gln Tyr Thr Ser Arg Asp Ser Phe Lys Ala Phe Ala
385                 390                 395                 400

Lys Ala Leu Gly Val Met Asp Asp Leu Lys Ser Gly Val Pro Arg Ala
                405                 410                 415

Gly Tyr Arg Gly Val Val Thr Phe Gln Phe Arg Gly Arg Arg Val His
                420                 425                 430

Leu Ala Pro Pro Gln Thr Trp Glu Gly Tyr Asp Pro Ser Trp Asn
            435                 440                 445
```

CHINESE HAMSTER OVARY CELL LINES

CROSS REFERENCE TO RELATED APPLICATIONS

This application is a divisional of copending U.S. patent application Ser. No. 13/119,461, filed Mar. 17, 2011, which is a 35 U.S.C. §371 National Phase Entry application of International Application No. PCT/SG2009/000348 filed on Sep. 18, 2009, which designates the United States, and which claims the benefit of priority under 35 U.S.C. §119(e) of U.S. Provisional Application No. 61/098,270 filed on Sep. 19, 2008, and U.S. Provisional Application No. 61/183,647 filed on Jun. 3, 2009, the contents of each of which are herein incorporated by reference in their entireties.

The foregoing applications, and each document cited or referenced in each of the present and foregoing applications, including during the prosecution of each of the foregoing applications ("application and article cited documents"), and any manufacturer's instructions or catalogues for any products cited or mentioned in each of the foregoing applications and articles and in any of the application and article cited documents, are hereby incorporated herein by reference. Furthermore, all documents cited in this text, and all documents cited or reference in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

FIELD

This invention relates to the fields of biotechnology and molecular biology. The invention in particular relates to Chinese Hamster Ovary cell lines and their use in recombinant protein expression.

BACKGROUND

Proteins are useful in a variety of diagnostic, pharmacologic, agricultural, nutritional, and research applications. Given the high cost of producing proteins, especially therapeutic proteins, even small increases in the efficiency of production or in the function and stability of a protein can be valuable.

The function and stability, and hence the utility, of a protein can be affected by the post-translational addition of sugar residues to the protein to form a glycoprotein. For example, the addition of terminal sialic acid residues to polysaccharides attached to a glycoprotein generally increases the protein's lifetime in the bloodstream and can, in particular cases, also affect solubility, thermal stability, resistance to protease attack, antigenicity, and specific activity of some glycoproteins. See e. g. Gu and Wang (1998), Biotechnol. and Bioeng. 58 (6): 642-48; Morell et al. (1968), J. Biol. Chem. 243 (1): 155-59.

Recombinant glycoprotein proteins and drugs produced by cell lines, such as Chinese hamster ovary (CHO) cells, generally consist of differentially sialylated isoforms. Poorly sialylated isoforms have shorter circulatory half-life and are thus less efficacious.

It is therefore desirable to increase the sialic acid content of a glycoprotein, especially a glycoprotein to be used for pharmacologic applications. Indeed, one of the major research focuses in the biotechnology field has been how to increase sialylation of recombinant protein drugs.

SUMMARY

According to a $1^{st}$ aspect of the present invention, we provide a Chinese Hamster Ovary (CHO) cell which is capable of higher protein sialylation compared to a wild type Chinese Hamster Ovary cell, in which the CHO cell is obtainable by selection with *Ricinus communis* agglutinin I (RCA-I). The CHO cell may be capable of higher sialylation in the presence of functional GnT 1.

The CHO cell may comprise a mutation in the GnT 1 gene.

The mutation in the GnT 1 gene may comprise one or more of the following mutations at the specified position of a GnT 1 sequence (GenBank accession number: AF343963): (a) a C to T transition at position 1015; (b) a G to C transversion at position 1300; (c) an A to C transversion at position 638; (d) a C to G transversion at position 784; (e) a T to A transversion at position 811; (f) an insertion at position 706 resulting in a frame shift from position 236 of the encoded amino acid sequence; (g) a C to T transition at position 1015; (h) a G to A transition at position 246; (i) a G to A transition at position 258; (j) an A to T transversion at position 859.

The GnT 1 gene may comprise a GnT 1 nucleic acid sequence shown in SEQ ID NO: 1.

The CHO cell may express a GnT 1 protein comprising one or more of the following mutations at the specified position of a GnT 1 sequence (GenBank accession number: AF343963): (a) Ala to Pro at position 434; (b) Asp→Ala at position 213; (c) Arg→Gly at position 262; (d) Trp→Arg at position 271; (e) frame shift from position 236 resulting from an insertion at position 706 of an encoding GnT 1 nucleic acid sequence; (f) Gln→STOP at position 339; (g) Trp→STOP at position 82; (h) Trp→STOP at position 86; (i) Lys→STOP at position 287.

The CHO cell may express a GnT 1 protein as shown in SEQ ID NO: 2.

The CHO cell may comprise a nucleic acid sequence encoding a protein of interest such as a recombinant protein of interest. The protein of interest may comprise erythropoietin (EPO) or interferon-γ (IFN-γ).

The CHO cell may comprise a nucleic acid sequence encoding functional GnT 1. The nucleic acid sequence encoding the protein of interest and the nucleic acid sequence encoding functional GnT 1 may be comprised in one expression vector.

The nucleic acid sequence encoding the protein of interest and the nucleic acid sequence encoding functional GnT 1 may be stably transfected into the CHO cell.

There is provided, according to a $2^{nd}$ aspect of the present invention, a CHO cell line comprising a CHO cell according to the $1^{st}$ aspect of the invention.

The CHO cell line may comprise a JW152 cell line (deposited at ATCC under the Budapest Treaty as accession number PTA-9657), a JW80 cell line, a JW36 cell line, a KFC15002 cell line, a KFC15071 cell line, a KFC5008 cell line, a JW152 cell line, a KFC5026 cell line, a KFC20011 cell line or a KFC15047 cell line.

The CHO cell or a CHO cell line may be is adapted to suspension culture.

We provide, according to a $3^{rd}$ aspect of the present invention, a recombinant protein expressed by a CHO cell or CHO cell line according to the $1^{st}$ or $2^{nd}$ aspect of the invention.

The recombinant protein may comprise erythropoietin (EPO) or interferon-γ (IFN-γ).

The recombinant protein may comprise a pKa of 4 or less, 3.5 or less, 3 or less, 2.5 or less or 2 or less or a Z-number of greater than 150, such as greater than 160, greater than 170, greater than 180, such as greater than 190, greater than 200, greater than 210, such as greater than 220 or greater than 230, or both.

As a 4th aspect of the present invention, there is provided a method of expressing a recombinant protein, the method comprising introducing a nucleic acid encoding the protein into a CHO cell as set out above, allowing the protein to be expressed from the CHO cell or a descendent thereof, and optionally purifying the protein.

The method may comprise introducing a nucleic acid encoding functional GnT 1 into the CHO cell.

The method may comprise introducing an expression vector comprising a nucleic acid sequence encoding the protein and a nucleic acid sequence encoding functional GnT 1.

The method may comprise stably transfecting the nucleic acid sequence encoding the protein of interest and the nucleic acid sequence encoding functional GnT 1.

We provide, according to a 5th aspect of the present invention, a nucleic acid comprising a sequence shown in SEQ ID NO: 1, or a sequence comprising a GnT 1 sequence together with a mutation set out in Column 2 of Table D1, or a variant, homologue, derivative or fragment thereof.

The present invention, in a 6th aspect, provides a polypeptide comprising a sequence as shown in SEQ ID NO: 2, or a sequence comprising a GnT 1 sequence together with a mutation set out in Column 3 of Table D1, or a variant, homologue, derivative or fragment thereof.

In a 7th aspect of the present invention, there is provided a method of providing a CHO cell or cell line, the method comprising culturing CHO cells in the presence of *Ricinus communis* agglutinin I (RCA-I) and selecting cells which survive the culture.

The method may comprise culturing CHO cells in the presence of *Ricinus communis* agglutinin I (RCA-I) and selecting cells which survive the culture.

The method may comprise exposing the CHO cells to RCA-I at a concentration of between 0.1 μg/ml to 100 μg/ml, for example up to 50 μg/ml or up to 20 μg/ml, such as 10 μg/ml or 5 μg/ml.

The method may comprise exposing the CHO cells to RCA-I for a period of from an hour, a few hours (such as 2, 3, 4, 5, 6, 7, 8, 9, 10, 11, 12), overnight, to a few days, such as 2 days or 3 days, such as overnight.

The method may comprise further comprising selecting cells which do not react with RCA-I in an agglutination test.

According to an 8th aspect of the present invention, we provide a CHO cell or CHO cell line obtainable by a method set out above.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

SEQUENCE LISTING

Figure 1:
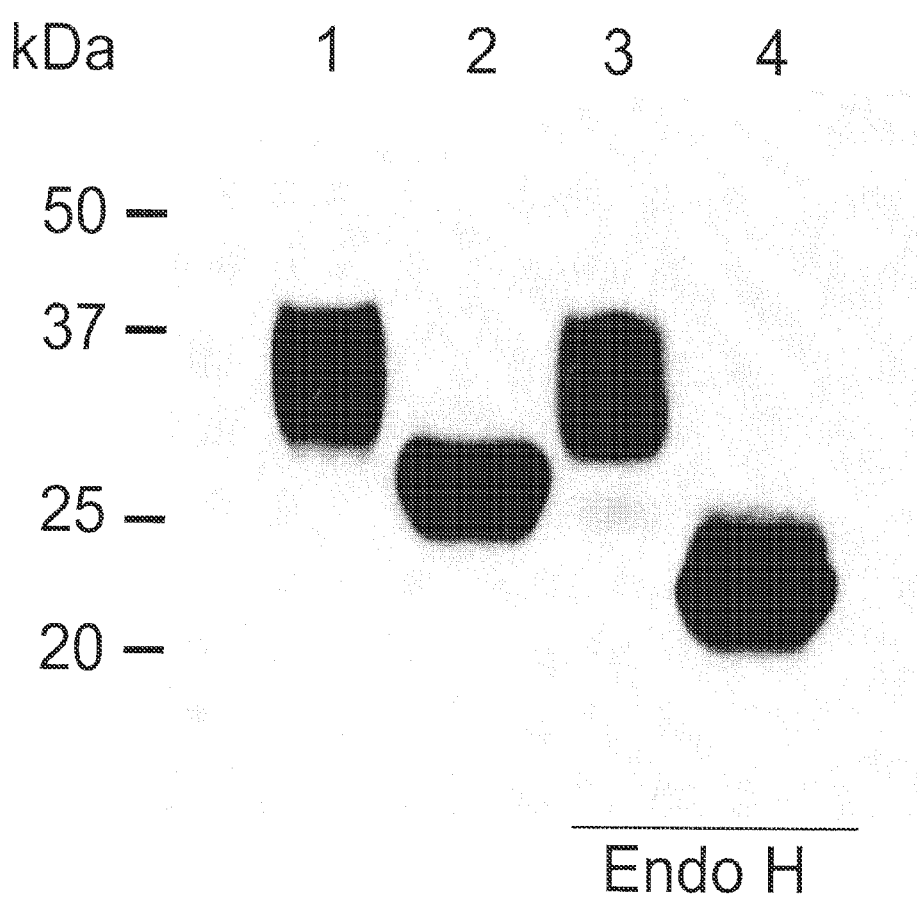
FIG. 1 is a photograph showing that transiently expressed erythropoietin (EPO) in JW152 cell line is sensitive to endoglucosidase H (Endo H) treatment. Western blot of transiently expressed EPO: from CHO K-1 cells (Lane 1), from JW152 cells (Lane 2), Endoglucosidase H treated EPO from CHO-K1 (Lane 3), Endoglucosidase H treated EPO from JW152 (Lane 4). JW152 expressed EPO is sensitive to Endo H treatment suggesting that the glycan structure found on the EPO molecule is of the high mannose type. It is hence suspected that gene(s) from the early part of the glycosylation pathway is defective.

SEQ ID NO: 1 is a nucleic acid sequence of a N-acetylglucoaminyltransferase I cDNA from CHO JW152 cells.

SEQ ID NO: 2 is an amino acid sequence of N-acetylglucoaminyltransferase I encoded by SEQ ID NO: 1.

DETAILED DESCRIPTION

Using a cytotoxic lectin, RCA-I, we have isolated a novel CHO mutant cell line, JW152, from CHO-K1 cells.

Recombinant EPO produced by JW152 cells that are stably transfected with EPO and GnT I cDNAs contains the highly sialylated isoforms. Several of these stably transfected lines have been adapted to suspension culture and grown in serum-free medium. The EPO produced by these cells are analyzed by an IEF assay. The results showed that EPO produced in serum-free medium remained highly sialylated.

These results suggest that JW152 cells have the potential to become a host cell line for producing proteins, such as highly sialylated proteins including glycoprotein drugs.

The cell line JW152 was deposited on 11 Dec. 2008 at the American Type Culture Collection, 10801 University Boulevard, Manassas, Va. 20110-2209, United States of America under the accession number PTA-9657 as the International Deposition Number under the Budapest Treaty on the International Recognition of the Deposit of Microorganisms for the Purposes of Patent Procedure.

We therefore provide for a Chinese Hamster Ovary (CHO) cell or cell line which is capable of higher protein sialylation compared to a wild type Chinese Hamster Ovary cell.

The CHO cell capable of higher sialylation may be produced by a suitable selection method such as a RCA-1 selection method. Such a method is described in further detail in "CHO Cells and Cell Lines" below. Therefore, RCA-I can be used to isolate CHO glycosylation mutant cells produce highly sialylated recombinant proteins in the presence of GnT I.

Such a selection method is therefore specifically included in the methods and compositions described here.

We therefore provide for a Chinese Hamster Ovary (CHO) cell or cell line which is capable of higher protein sialylation compared to a wild type Chinese Hamster Ovary cell, the CHO cell being obtainable by selection with *Ricinus communis* agglutinin I (RCA-I). In general, we provide a RCA-I resistant CHO cell or cell line, such as an RCA-I resistant CHO-K1 cell or cell line.

Genetic analysis has revealed a dysfunctional N-Acetylglucosaminyltransferase I (GnT I) gene in JW152 cells. Molecular cloning of the GnT I cDNA from the mutant cells identified a point mutation that results in a premature stop codon. As a result, the JW152 cells can only synthesize a truncated version of GnT I protein with only 338 amino acids, rather than the normal protein which contains 447 amino acids.

Using RCA-I we have isolated many more CHO mutant lines (about 100 clones). Genetic analyses showed that they all lack functional GnT I gene. Many of them carry a different point mutation in the coding region of GnT I gene, suggesting that they derived from different original clones. Yet, they all dramatically improved sialylation of recombinant proteins in the presence of GnT I. The mutations in the GnT 1 genes from these further CHO cell lines are shown in Table D1 below.

Accordingly, we provide for a Chinese Hamster Ovary (CHO) cell which is capable of higher protein sialylation in the presence of functional GnT 1 compared to a wild type Chinese Hamster Ovary cell, the CHO cell comprising a mutation in the GnT 1 gene. We further provide for a Chinese Hamster Ovary (CHO) cell or cell line which is capable of higher protein sialylation compared to a wild type Chinese Hamster Ovary cell, the CHO cell being obtainable by selection with *Ricinus communis* agglutinin I (RCA-I) and comprising a mutation in the GnT 1 gene.

The mutation in the GnT 1 gene may comprise any point mutation, deletion, inversion, etc. The mutation in the GnT 1 gene may encode a partially functioning, or non-functioning GnT 1 polypeptide. The mutation in the GnT 1 gene may encode a truncated GnT 1 polypeptide.

We provide for CHO cells and cell lines comprising each of these mutant CHO cell lines and clones. We provide for specific cell lines derived from RCA-I selection and capable of higher sialylation compared to wild type or native CHO cells or parental cells. We provide for mutant CHO nucleic acid and polypeptide sequences comprised in such cells or cell lines, as described in further detail below.

The CHO cell or cell line may comprise a JW152 cell line. It may comprise a JW80 cell line. It may comprise a JW36 cell line. It may comprise a KFC15002 cell line. It may comprise a KFC15071 cell line. It may comprise a KFC5008 cell line. It may comprise a JW152 cell line. It may comprise a KFC5026 cell line. It may comprise a KFC20011 cell line. It may comprise a KFC15047 cell line.

The CHO cell or cell line may be transfected with a nucleic acid encoding a protein of interest, for example a heterologous or recombinant protein. Such a protein might comprise a glycoprotein. The CHO cell or cell line may be transfected or co-transfected with a nucleic acid encoding a functional or full length or wild type GnT 1 sequence.

As noted above, we provide for the nucleic acid themselves, e.g., a nucleic acid encoding a mutant GnT 1 gene, or a fragment, variant, derivative or homologue of such a nucleic acid. The nucleic acid encoding a mutant GnT 1 gene, fragment, variant, derivative or homologue may cause a CHO cell comprising it to be capable of higher sialylation, compared to a CHO cell which does not comprise such a nucleic acid, for example a wild type CHO cell. The nucleic acid encoding the mutant GnT 1 gene may comprise a sequence shown as SEQ ID NO: 1 or a variant, homologue, derivative or fragment thereof.

SEQ ID NO: 1

The coding region of N-acetylglucoaminyltransferase I (Mgat1, GenBank: AF343963) mRNA isolated from the CHO JW152 cells. In these mutant cells, a C to T point mutation at position 1015 was identified (shown in bold):

ATGCTGAAGAAGCAGTCTGCAGGGCTTGTGCTTTGGGGTGCTATCCTCTT

TGTGGGCTGGAATGCCCTGCTGCTCCTCTTCTTCTGGACACGCCCAGCCC

CTGGCAGGCCCCCCTCAGATAGTGCTATCGATGATGACCCTGCCAGCCTC

ACCCGTGAGGTGTTCCGCCTGGCTGAGGACGCTGAGGTGGAGTTGGAGCG

GCAGCGGGGGCTGTTGCAGCAAATCAGGGAGCATCATGCTTTGTGGAGAC

AGAGGTGGAAAGTGCCCACCGTGGCCCCTCCAGCCTGGCCCCGTGTGCCT

GCGACCCCCTCACCAGCCGTGATCCCCATCCTGGTCATTGCCTGTGACCG

CAGCACTGTCCGGCGCTGCTTGGATAAGTTGTTGCACTATCGGCCCTCAG

CTGAGCATTTCCCCATCATTGTCAGCCAGGACTGCGGGCACGAAGAGACA

GCACAGGTCATTGCTTCCTATGGCAGTGCAGTCACACACATCCGGCAGCC

AGACCTGAGTAACATCGCTGTGCCCCAGACCACCGCAAGTTCCAGGGTT

ACTACAAGATCGCCAGGCACTACCGCTGGGCACTGGGCCAGATCTTCAAC

AAGTTCAAGTTCCCAGCAGCTGTGGTAGTGGAGGACGATCTGGAGGTGGC

ACCAGACTTCTTTGAGTACTTCCAGGCCACCTACCCACTGCTGAGAACAG

ACCCCTCCCTTTGGTGTGTGTCTGCTTGGAATGACAATGGCAAGGAGCAG

ATGGTAGACTCAAGCAAACCTGAGCTGCTCTATCGAACAGACTTTTTTCC

TGGCCTTGGCTGGCTGCTGATGGCTGAGCTGTGGACAGAGCTGGAGCCCA

AGTGGCCCAAGGCCTTCTGGGATGACTGGATGCGCAGACCTGAGCAGCGG

AAGGGGCGGGCCTGTATTCGTCCAGAAATTTCAAGAACGATGACCTTTGG

CCGTAAGGGTGTGAGCCATGGGCAGTTCTTTGATCAGCATCTTAAGTTCA

TCAAGCTGAACCAGTAGTTCGTGTCTTTCACCCAGTTGGATTTGTCATAC

TTGCAGCGGGAGGCTTATGACGGGATTTCCTTGCCCGTGTCTATAGTGC

CCCCCTGCTACAGGTGGAGAAAGTGAGGACCAATGATCAGAAGGAGCTGG

GGGAGGTGCGGGTACAGTACACTAGCAGAGACAGCTTCAAGGCCTTTGCT

AAGGCCCTGGGTGTCATGGATGACCTCAAGTCTGGTGTCCCCAGAGCTGG

CTACCGGGGCGTTGTCACTTTCCAGTTCAGGGGTCGACGTGTCCACCTGG

CACCCCCACAAACCTGGGAAGGCTATGATCCTAGCTGGAATTAG

We further provide for mutant GnT 1 polypeptides, as well as fragments, variants, derivatives and homologoues thereof. The mutant GnT 1 polypeptide, fragment, variant, derivative or homologue may cause a CHO cell comprising it to be capable of higher sialylation, compared to a CHO cell which does not comprise such a polypeptide, for example a wild type CHO cell. The mutant GnT 1 polypeptide may comprise a sequence shown as SEQ ID NO: 2 or a variant, homologue, derivative or fragment thereof.

SEQ ID NO: 2

The N-acetylglucoaminyltransferase I (GnT I) protein encoded by the mutated gene in CHO JW152 cells. As a result of the point mutation (C1015T), JW152 cells only produce a truncated version of GnT I which contains only 338 amino acids rather than the normal protein that contains 447 amino acids. The C-terminal portion in bold is not translated in JW152 cells.

MLKKQSAGLVLWGAILFVGWNALLLLFFWTRPAPGRPPSDSAIDDDPASL

TREVFRLAEDAEVELERQRGLLQQIREHHALWRQRWKVPTVAPPAWPRVP

ATPSPAVIPILVIACDRSTVRRCLDKLLHYRPSAEHFPIIVSQDCGHEET

AQVIASYGSAVTHIRQPDLSNIAVPPDHRKFQGYYKIARHYRWALGQIFN

KFKFPAAVVVEDDLEVAPDFFEYFQATYPLLRTDPSLWCVSAWNDNGKEQ

MVDSSKPELLYRTDFFPGLGWLLMAELWTELEPKWPKAFWDDWMRRPEQR

KGRACIRPEISRTMTFGRKGVSHGQFFDQHLKFIKLNQQFVSFTQLDLSY

-continued
LQREAYDRDFLARVYSAPLLQVEKVRTNDQKELGEVRVQYTSRDSFKAFA

KALGVMDDLKSGVPRAGYRGVVTFQFRGRRVHLAPPQTWEGYDPSWN

Figure 2:
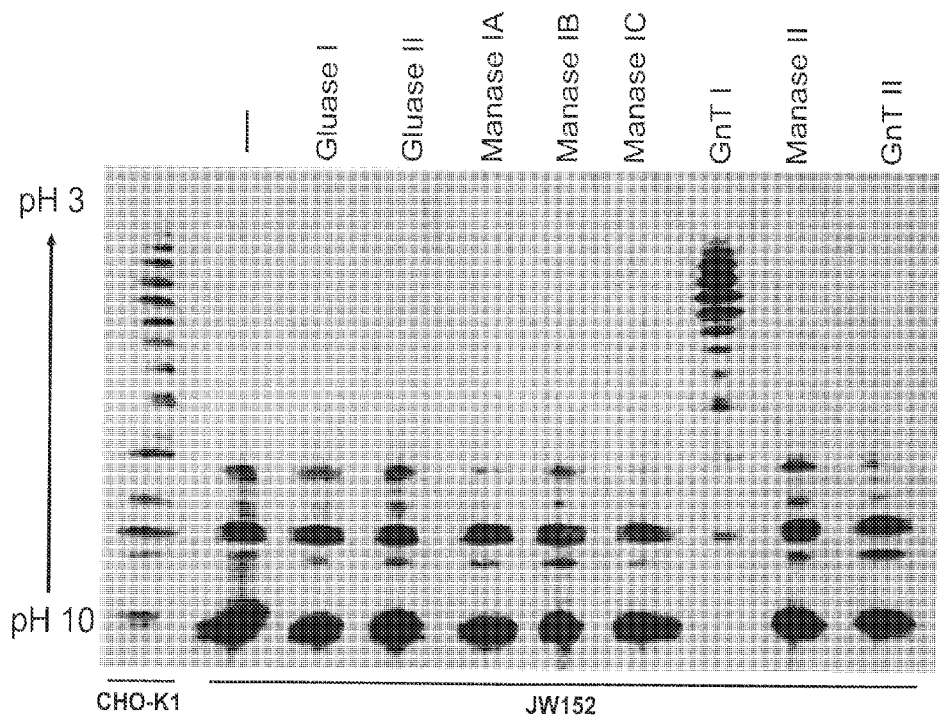
FIG. 2 is a photograph showing that JW152 cells lack a functional GnT I gene. Recombinant EPO is analyzed by the IEF/Western blot assay. The lane on the far left (CHO WT) shows the EPO expressed by the wild type CHO cells as a control. The second lane shows the EPO produced by the JW152 cells. Incomplete glycosylation in JW152 cells is obvious by comparing the two lanes. For the complementation test, each of several glycosylation related genes (as indicated) is co-transfected with the EPO construct into JW152 cells. Only GnT I is able to complement the genetic defect in JW152 cells, suggesting these cells lack a functional GnT I gene. Another very important observation from this IEF results is that in the presence of GnT I, JW152 cells sialylate EPO much better than the wild type cells.

Several of the JW152-pEIG stable lines shown in FIG. 2 have been adapted in suspension culture and grown in serum-free medium. The EPO produced in serum-free medium remained highly sialylated. We therefore provide for mutant CHO cells and cell lines derived from RCA-I selection, which have been adapted to suspension culture, or growth in semi-solid medium.

In conclusion, we have developed a novel method to isolate glycosylation mutant cells from CHO cells. All CHO cells that survive RCA-I treatment have very similar characteristics. First, they all lack a functional GnT I gene. Second, they all sialylate their recombinant proteins better than the wild type CHO cells in the presence of GnT I. This feature remains the same both in transient transfection and in stably transfected cells.

The CHO glycosylation mutant cells isolated with RCA-I, such as JW152 cells, can produce recombinant glycoproteins with high degree of sialylation as long as GnT I is present. This method can be used to produce recombinant glycoproteins in which sialic acid content is important for the efficacy. These proteins include EPO, IEF-γ, Factor VIII etc.

CHO Cells and Cell Lines

The CHO cells and cell lines described here may be made by any suitable means. For example, the CHO cells and cell lines may be produced by selection using a suitable agglutinating agent, such as agglutinin I The agglutinin may comprise any suitable agglutinin, such as *Ricinus communis* agglutinin I (RCA-I).

We therefore provide a method of providing a CHO cell or cell line, the method comprising culturing CHO cells in the presence of *Ricinus communis* agglutinin I (RCA-I) and selecting cells which survive the culture.

The CHO cells and cell lines described here may be made by treating a starting or parent cell with *Ricinus communis* agglutinin I (RCA-I) and selecting cells that survive such treatment. Such surviving cells may be further cloned and made into cell lines. The selected cells and cell lines may comprise higher sialylation activity as described in this document. The selected cells and cell lines may comprise mutant GnT 1 genes and polypeptides, as described in this document.

For example, the CHO cells or cell lines described here may be selected by exposing a parent cell line to *Ricinus communis* agglutinin I (RCA-I) at a suitable concentration for a suitable period.

The RCA-1 concentration could range from between 0.1 μg/ml to 100 μg/ml, for example up to 50 μg/ml or up to 20 μg/ml. Examples of specific concentrations include 10 μg/ml and 5 μg/ml.

The period of incubation or exposure to RCA-1 could be from an hour, a few hours (such as 2, 3, 4, 5, 6, 7, 8, 9, 10, 11, 12), overnight, to a few days, such as 2 days or 3 days.

In general, the period and concentration can be adjusted to eliminate the majority of CHO cells, but to enable a small proportion of cells, which are resistant to RCA-I, to survive and form colonies. Within this, the concentration and period of exposure and selection may be varied, but generally, the higher the concentration of RCA-I, the lower the period of exposure is necessary, and vice versa.

The selection could be done on any suitable starting cell or cell line, but this will generally be a CHO cell or cell line. Any known CHO cell or cell line could be used as a starting point or parent cell, including CHO-K1. Other suitable starting cells could include, but are not limited to the following (ECACC accession numbers in brackets): CHO (85050302), CHO (PROTEIN FREE) (00102307), CHO-K1 (85051005), CHO-K1/SF (93061607), CHO/dhFr− (94060607), CHO/dhFr-AC-free (05011002), RR-CHOKI (92052129).

Following selection, the surviving cells are allowed to grow and form colonies following which they may be picked. The time allowed for this will vary, but will generally be long enough for colonies to grow to a pickable size. Examples of such times are 5 days, 7 days, 9 days, 11 days, 13 days, one week, two weeks, three weeks or more.

The picking may be done manually, or it may be automated through use of robots, such as CLONEPIX (Genetix, New Milton, Hampshire, UK). The picked colonies may be further cloned, further screened, characterised and cultured, etc.

The selected cells may be subjected to further tests. For example, they may be subjected to agglutination tests using RCA-I to confirm the mutant cells no longer react with RCA-I.

As a specific example, which is not intended to be limiting, CHO-K1 cells may be cultured, for example in 6-well plates, to confluence. Culture media may be changed to serum-free DMEM. *Ricinus communis* agglutinin I (RCA-I, EY Laboratories) may be added into the media to reach a final concentration of 10 μg/gml. This may be incubated with cells overnight. The serum-free DMEM containing RCA-I may be replaced, for example with fresh DMEM with 10% FBS. Nine days later, colonies of the CHO cells that survive the RCA-I treatment may be picked and cultured, for example in 24 well plates.

These cells may be subjected to further tests, such as agglutination tests using RCA-I to confirm the mutant cells no longer react with RCA-I. We therefore provide for a method of providing a CHO cell or cell line, the method comprising culturing CHO cells in the presence of *Ricinus communis* agglutinin I (RCA-I), selecting cells which survive the culture and which do not react with RCA-I in an agglutination test.

The RCA-I selected CHO cells and CHO cell lines may be tested for their sialylation behaviour, by for example expressing a protein of interest and determining the degree of sialylation. This may be done by the methods described in "Sialylation" below.

We therefore provide for a method of providing a CHO cell or cell line, the method comprising culturing CHO cells in the presence of *Ricinus communis* agglutinin I (RCA-I), selecting cells which survive the culture and selecting those cells or cell lines which display high sialylation behaviour, for example high Z-number or low pI of expressed proteins.

The GnT 1 gene in such selected cells may be cloned and sequenced, using methods known in the art. The GnT 1 gene may comprise a mutant GnT 1 gene as described here.

We therefore provide for a method of providing a CHO cell or cell line, the method comprising culturing CHO cells in the presence of *Ricinus communis* agglutinin I (RCA-I), selecting cells which survive the culture and selecting those cells or cell lines which comprise mutant GnT 1 genes as described herein.

Mutant CHO Cells and Cell Lines

We provide for a CHO cell or cell line derived from RCA-I selection, as described above. Such a cell line could include a JW152 cell line, or any of the cell lines set out in Table D1 below, including a JW80 cell line, a JW36 cell line, a KFC15002 cell line, a KFC15071 cell line, a KFC5008 cell line, a JW152 cell line, a KFC5026 cell line, a KFC20011 cell line or a KFC15047 cell line.

Protein Expression

The CHO cells described here may be used as host cells for expression of any protein of interest. This may be done by means known in the art.

Protein expression in CHO cells and cell lines is well described in the literature, and the skilled person will have little difficulty in using the CHO cells and cell lines described here as hosts for protein expression. Thus, for example, the CHO cells and cell lines may be transfected by means known in the art with expression vectors capable of expressing the protein of interest.

The CHO cells and cell lines may further be capable of expressing wild type or functional GnT 1, for example, the sequence set out in GenBank accession number AF343963. This may be done by transfecting the CHO cells and cell lines with an expression vector encoding GnT 1. This may be on the same or different vector as that which contains the nucleic acid encoding the protein of interest Any suitable protein may be expressed using the CHO cells described here as host cells. The protein may comprise a heterologous protein. The protein may comprise a recombinant protein. The protein may comprise an engineered protein. The protein may comprise a glycoprotein.

Examples include heterologous proteins of therapeutic or pharmacological interest. Proteins which may be expressed include anti-EGFR mAb, α-glucosidase, laronidase, Ig-CTLA4 fusion, N-acetylgalactosamine-4-sulfatase, luteinizing hormone, anti-VEGF mAb, Factor VIII, anti-lgE mAb, anti-CD11a mAb, α-galactosidase, interferon-β, anti-TNFα mAb, erythropoietin, anti-CD52 mAb, Factor VIII, tissue plasminogen activator, anti-HER2 mAb, TNFα receptor fusion, Factor IX, follicle stimulating hormone, anti-CD20 mAb, interferon-β, β-glucocerebrosidase, deoxyribonuclease I, etc.

For example, we describe the expression of erythropoietin (EPO), interferon-γ and Factor VIII with CHO cells and cell lines described here. We also describe highly sialylated forms or isoforms of erythropoietin (EPO), interferon-γ and Factor VIII expressed from CHO cells and cell lines described here.

Sialic Acid

The term "sialic acid" is intended to refer to any member of a family of nine-carbon carboxylated sugars.

The most common member of the sialic acid family is N-acetylneuraminic acid (2-keto-5-acetamido-3,5-dideoxy-D-glycero-D-galactononulopyranos-1-onic acid, often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sciatic acid family member is 2-keto-3-deoxy-nonulosonic acid (KDN). 17

Also included are 9-substituted sialic acids such as a 9-O-C1-C6-acyl-Neu5Ac like 9-0-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e. g., Varki; Glycobiology 2 1992; 25-40; Sialic Acids: Chemistry, Metabolism and Function, R. Schauer, Ed.

Sialylation

The degree of sialylation of a protein may be measured by various means, such as using Z-numbers or expressing the isoelectric point of the protein.

We therefore provide for protein expression using the CHO cells and cell lines described here, such protein expression comprising highly sialylated forms or isoforms of proteins of interest. Protein expression from CHO cells and CHO cell lines described here enables production of proteins such as glycoproteins, for example erythropoietin (EPO), interferon-γ and Factor VIII, which have high Z-numbers or low pIs, or both.

Z-Number

The parameter Z-number provides a measure of how many of the antennae of the carbohydrate moieties in a glycoprotein bear charged residues, such as sialic acid.

To determine Z-number, the carbohydrate moieties are released from the peptide, as above, and labelled, if desired. The mixture is then separated by ion exchange chromatography, allowing the separation of species on the basis of charge. Visualisation of the eluted peaks may be by virtue of a label, as mentioned above, or may be by some other method, such as mass-spectrometry.

A chromatogram is then analysed by integrating the peaks associated with mono-di-tri- and tetra-charged carbohydrate species. The percentage of the total carbohydrate represented by each species can then be used to calculate Z-number according to the following equation: $Z = P'mono + 2\, P'di + 3\, P'tri + 4\, P'tetra$ wherein Z is Z-number, and P'mono, P'di, P'tri and P'tetra are the percentage of total carbohydrate that is mono-, di-, tri- and tetra-charged respectively.

A high Z-number indicates that a large number of antennae bear charged residues, and that the glycoprotein will therefore be highly charged, and in the case of sialic acid residues, acidic.

The CHO cells described here are capable of expressing proteins with a high degree of sialylation. Thus, for example, the CHO cells may express proteins with high Z-number values such as greater than 150, such as greater than 160, greater than 170, greater than 180, such as greater than 190, greater than 200, greater than 210, such as greater than 220, greater than 230, etc.

Isoelectric Point

The isoelectric point (pI) of a protein may also be used as a measure of its sialylation. The higher the degree of sialylation, the more acidic it is and the lower its pI.

Proteins expressed by the CHO cells described here have significantly lower pi profiles than their normal counterparts, e.g., native proteins, or counterpart proteins expressed by wild type CHO cells. For example, the proteins expressed by the CHO cells and cell lines described here may have low pIs, such as pIs of 4.5 or less, such as 4.3 or less, 4.1 or less, 4.0 or less, 3.8 or less, 3.6 or less, 3.4 or less, 3.2 or less, 3.0 or less, 2.8 or less, 2.6 or less, etc. The pIs may be of individual protein molecules, or a batch or fraction of them, or an average pI of an expressed lot of protein.

The expressed proteins may be isolated from a mixture of isoforms using a number of methods that will be known to one skilled in the art. For example, isoelectric focussing, chromatofocussing or ion-exchange chromatography may be used to separate the isoforms on the basis of pI. The different fractions can be analysed for sialic acid content, and the desired fractions selected for use.

Mutant GnT 1 Sequences

We disclose mutant GnT 1 sequences comprising mutant GnT 1 amino acid sequences and mutant GnT1 nucleic acid sequences.

Example mutant GnT 1 amino acid sequences include the sequence shown as SEQ ID NO: 2, as well as the sequences comprising the mutations shown in column 3 of Table D1 below.

Example mutant GnT 1 nucleic acid sequences include the sequence shown as SEQ ID NO: 1, as well as the sequences comprising the mutations shown in column 2 of Table D1 below.

Table D1 shows the mutations in the GnT 1 sequence of clones isolated from selection with RCA-I, as described in the Examples below.

Corresponding mutations are tabulated alongside showing respective nucleotide and amino acid mutation and possible location of the disruption in secondary structure/interaction or the resulting loss in amino acids in the case of a stop codon mutation.

A minimum of 4 bacteria colonies were sequenced to ensure that the mutations found were not due to PCR error.

TABLE D1

Table of mutations found in GnT1 mutants from clones derived from RCA-I screening (Example 10 below). Nine CHO glycosylation mutants with different mutations in the GnT1 gene. Point mutations leading to loss in function were found in four cell lines (JW80, JW36, KFC15002, KFC15071). A point insertion resulting in the generation of a stop codon was found in KFC 5008. Mutations leading to a premature stop codon were also found in another four cell lines. (JW152, KFC5026, KFC20011, KFC15047).

| Mutant CHO Cell Line | DNA Mutation | Polypeptide Mutation (position, mutation) | Comment |
|---|---|---|---|
| JW80 | G1300C | Position 434 Ala →Pro | Domain 2 β14 |
| JW36 | A638C | Position 213 Asp → Ala | Disruption of DxD Motif, similar to JW98, JW191 |
| KFC15002 | C784G | Position 262 Arg →Gly | Domain 1 β6, similar to KFC15008 (aka 15008), KFC7501 (aka 7501) and KFC12008 |
| KFC15071 | T811A | Position 271 Trp → Arg | Domain 1 β7 |
| KFC5008 | _706C | Insertion at 706 bp Frame shift from 236 aa Asp→STOP | Stop codon generated at 245 a.a. |
| JW152 | C1015T | Position 339 Gln→STOP | 108 a.a. missing from C terminal |
| KFC5026 | G246A | Position 82 Trp→STOP | 365 a.a. missing from C terminal |
| KFC20011 | G258A | Position 86 Trp→STOP | 361 a.a. missing from C terminal |
| KFC15047 | A859T | Position 287 Lys→STOP | 160 a.a. missing, similar to KFC15026 and KFC15072 |

Mutant GnT 1 Polypeptides

The CHO cells and cell lines comprise mutant GnT 1 polypeptides.

We therefore provide generally for a mutant GnT 1 polypeptide, together with fragments, homologues, variants and derivatives thereof. These polypeptide sequences may comprise the polypeptide sequences disclosed here, and particularly in the sequence listings.

The mutant GnT 1 polypeptide may comprise one or more changes compared to the wild type GnT 1 sequence. Such mutations may result from stop codons being introduced in the encoding nucleic acid sequence and consequent premature termination of translation of the GnT 1 mRNA.

The mutant GnT 1 polypeptide may be shorter than a wild type GnT 1 polypeptide. It may be a truncated version of wild type GnT 1 polypeptide. The length of the mutant GnT 1 polypeptide may be 90% or less, 80% or less, 70% or less, etc than the wild type sequence.

For example, a mutant GnT 1 polypeptide may be missing 5, 10, 15, 20, 25, 30, 35, 40, 45, 50, 55, 60, 65, 70, 75, 80, 85, 90, 95, 100 or more C-terminal residues compared to full length or wild type GnT 1 polypeptide.

The mutant GnT 1 polypeptide may for example comprise a sequence set out in SEQ ID NO: 2. This is the mutant GnT 1 polypeptide sequence from the cell line JW152. The mutant GnT 1 polypeptide may comprise a GnT 1 sequence comprising a mutation set out at column 3 of Table D1 above.

It will be understood that the mutant GnT 1 polypeptide sequences disclosed here are not limited to the particular sequences set forth in the sequence listing, or fragments thereof, or sequences obtained from mutant GnT 1 protein, but also include homologous sequences obtained from any source, for example related cellular homologues, homologues from other species and variants or derivatives thereof, provided that they have at least one of the biological activities of mutant GnT 1, as the case may be.

This disclosure therefore encompasses variants, homologues or derivatives of the amino acid sequences set forth in the sequence listings, as well as variants, homologues or derivatives of the amino acid sequences encoded by the nucleotide sequences disclosed here. Such a sequences is generally referred to as a "mutant GnT 1 sequence".

The length of the mutant GnT 1 polypeptide may be 90% or less, 80% or less, 70% or less, etc than a corresponding wild type sequence.

For example, a mutant GnT 1 nucleic acid may encode a mutant GnT 1 polypeptide that is missing 5, 10, 15, 20, 25, 30, 35, 40, 45, 50, 55, 60, 65, 70, 75, 80, 85, 90, 95, 100 or more C-terminal residues.

Biological Activities

In some embodiments, the sequences comprise at least one biological activity of mutant GnT 1, as the case may be. The biological activity may comprise improved ability to express proteins with higher sialylation compared to wild type GnT 1

Homologues

The polypeptides disclosed include homologous sequences obtained from any source, for example related viral/bacterial proteins, cellular homologues and synthetic peptides, as well as variants or derivatives thereof.

In the context of the present document, a homologous sequence or homologue is taken to include an amino acid sequence which is at least 60, 70, 80 or 90% identical, such as at least 95 or 98% identical at the amino acid level over at least 30, such as 50, 70, 90 or 100 amino acids with GnT 1, as the case may be, for example as shown in the sequence listing herein. In the context of this document, a homologous sequence is taken to include an amino acid sequence which is at least 15, 20, 25, 30, 40, 50, 60, 70, 80 or 90% identical, such as at least 95 or 98% identical at the amino acid level, such as over at least 15, 25, 35, 50 or 100, such as 200, 300, 400 or 500 amino acids with the sequence of GnT 1.

Although homology can also be considered in terms of similarity (i.e. amino acid residues having similar chemical properties/functions), in the context of the present document it is possible to express homology in terms of sequence identity. In some embodiments, the sequence identity is determined relative to the entirety of the length the relevant sequence, i.e., over the entire length or full length sequence of the relevant gene, for example.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, the default values may be used when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). The public default values for the GCG package, or in the case of other software, the default matrix, such as BLOSUM62 may be used.

Once the software has produced an optimal alignment, it is possible to calculate % homology, such as % sequence identity. The software typically does this as part of the sequence comparison and generates a numerical result.

Variants and Derivatives

The terms "variant" or "derivative" in relation to the amino acid sequences as described here includes any substitution of, variation of, modification of, replacement of, deletion of or addition of one (or more) amino acids from or to the sequence. For example, the resultant amino acid sequence retains substantially the same activity as the unmodified sequence, such as having at least the same activity as the mutant GnT 1 polypeptide shown in the sequence listings.

Polypeptides having the amino acid sequence shown in the Examples, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Amino acid substitutions may include the use of non-naturally occurring analogues, for example to increase blood plasma half-life of a therapeutically administered polypeptide.

Natural variants of mutant GnT 1 are likely to comprise conservative amino acid substitutions. Conservative substitutions may be defined, for example according to the Table below. Amino acids in the same block in the second column and in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Fragments

Polypeptides disclosed here and useful as markers also include fragments of the above mentioned full length polypeptides and variants thereof, including fragments of the sequences set out in the sequence listings.

Polypeptides also include fragments of the full length sequence of the mutant GnT 1 polypeptide. Such fragments may comprise at least one epitope. Methods of identifying epitopes are well known in the art. Fragments will typically comprise at least 6 amino acids, such as at least 10, 20, 30, 50 or 100 amino acids.

Included are fragments comprising, such as consisting of, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145 or 150, or more residues from a mutant GnT 1 amino acid sequence.

Polypeptide fragments of the mutant GnT 1 proteins and allelic and species variants thereof may contain one or more (e.g. 5, 10, 15, or 20) substitutions, deletions or insertions, including conserved substitutions. Where substitutions, deletion and/or insertions occur, for example in different species, such as less than 50%, 40% or 20% of the amino acid residues depicted in the sequence listings are altered.

Mutant GnT 1, and fragments, homologues, variants and derivatives, may be made by recombinant means. However, they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6xHis, GAL4 (DNA binding and/or transcriptional activation domains) and β-galactosidase. It may also be convenient to include a proteolytic cleavage site between the fusion protein partner and the protein sequence of interest to allow removal of fusion protein sequences. The fusion protein may be such that it does not hinder the function of the protein of interest sequence. Proteins may also be obtained by purification of cell extracts from animal cells.

The mutant GnT 1 polypeptide, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A mutant GnT 1 variant, homologue, fragment or derivative may also be in a substantially purified form, in which case it will generally comprise the protein in a preparation in which more than 90%, e.g. 95%, 98% or 99% of the protein in the preparation is a protein.

The mutant GnT 1 polypeptides variants, homologues, fragments and derivatives disclosed here may be labelled with a revealing label. The revealing label may be any suitable label which allows the polypeptide, etc to be detected. Suitable labels include radioisotopes, e.g. $^{125}I$, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

Mutant GnT 1 polypeptide, variants, homologues, fragments and derivatives disclosed here, optionally labelled, my also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The mutant GnT 1 polypeptides variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the mutant GnT 1 polypeptide, variants, homologues, fragments and derivatives disclosed here are expressed may be used in assay systems to identify candidate substances which interfere with or enhance the functions of the polypeptides in the cell.

Mutant GnT 1 Nucleic Acids

The CHO cells and cell lines comprise mutant GnT 1 nucleic acids.

We therefore provide generally for a mutant GnT 1 nucleic acid, together with fragments, homologues, variants and derivatives thereof. These nucleic acid sequences may encode the polypeptide sequences disclosed here, and particularly in the sequence listings.

The polynucleotide may comprise a mutant GnT 1 nucleic acid. The mutant GnT 1 nucleic acid may comprise one or more point mutations in the wild type GnT 1 sequence. Such mutations may result in corresponding changes to the amino acid sequence, or introduce stop codons and premature termination of translation of the GnT 1 mRNA.

The mutant GnT 1 nucleic acid may comprise a mutation resulting in a stop codon, which results in a mutant GnT 1 polypeptide being shorter than a wild type GnT 1 polypeptide. The length of the mutant GnT 1 polypeptide may be 90% or less, 80% or less, 70% or less, etc than the wild type sequence.

For example, a mutant GnT 1 nucleic acid may encode a mutant GnT 1 polypeptide that is missing 5, 10, 15, 20, 25, 30, 35, 40, 45, 50, 55, 60, 65, 70, 75, 80, 85, 90, 95, 100 or more C-terminal residues.

The mutant GnT 1 nucleic acid may for example comprise a sequence set out in SEQ ID NO: 1. This is the mutant GnT 1 nucleic acid sequence from the cell line JW152. The mutant GnT 1 nucleic acid may comprise a GnT 1 sequence comprising a mutation set out at column 2 of Table D1 above.

In particular, we provide for nucleic acids or polynucleotides which encode any of the GnT 1 polypeptides disclosed here. Thus, the term "GnT 1 sequence" should be construed accordingly. However, such a nucleic acid or polynucleotide may comprise a sequence set out as SEQ ID NO: 1, or a sequence encoding a of the corresponding polypeptide, and a fragment, homologue, variant or derivative of such a nucleic acid. The above terms therefore may be taken to refer to these sequences.

As used here in this document, the terms "polynucleotide", "nucleotide", and nucleic acid are intended to be synonymous with each other. "Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells.

"Polynucleotide" also embraces relatively short polynucleotides, often referred to as oligonucleotides.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Mutant GnT 1 Variants, Derivatives and Homologues

The mutant GnT 1 polynucleotides described here may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present document, it is to be understood that the polynucleotides described herein may be modified by any method available in the art. Such modifications may be carried out in order to enhance the in vivo activity or life span of polynucleotides.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

The terms "variant", "homologue" or "derivative" in relation to a nucleotide sequence include any substitution of, variation of, modification of, replacement of, deletion of or addition of one (or more) nucleotides from or to the sequence. The resulting sequence may be capable of encoding a polypeptide which is capable of mediating higher sialylation in a CHO cell.

As indicated above, with respect to sequence identity, a "homologue" has for example at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to the relevant sequence shown in the sequence listings.

There may be at least 95% identity, such as at least 96% identity, such as at least 97% identity, such as at least 98% identity, such as at least 99% identity. Nucleotide homology comparisons may be conducted as described above. A sequence comparison program that may be used is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

In some embodiments, a mutant GnT 1 polynucleotide has at least 90% or more sequence identity to a sequence shown as SEQ ID NO: 1. The mutant GnT 1 polynucleotide may have 60% or more, such as 65% or more, 70% or more, 75% or more, 80% or more, 85% or more, 90% or more, 95% or more, 97% or more or 98% or more sequence identity to a sequence shown as SEQ ID NO: 1.

Hybridisation

We further describe mutant GnT 1 nucleotide sequences that are capable of hybridising selectively to any of the sequences presented herein, or any variant, fragment or derivative thereof, or to the complement of any of the above. Nucleotide sequences are such as at least 15 nucleotides in length, such as at least 20, 30, 40 or 50 nucleotides in length.

The term "hybridisation" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, will be generally at least 70%, such as at least 80 or 90% or such as at least 95% or 98% homologous to the corresponding nucleotide sequences presented herein over a region of at least 20, such as at least 25 or 30, for instance at least 40, 60 or 100 or more contiguous nucleotides.

The term "selectively hybridisable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screened. In this event, background implies a level of signal generated by interaction between the probe and a non-specific DNA member of the library which is less than 10 fold, such as less than 100 fold as intense as the specific interaction observed with the target DNA. The intensity of interaction may be measured, for example, by radiolabelling the probe, e.g. with $^{32}P$.

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical polynucleotide sequences while an intermediate (or low) stringency hybridisation can be used to identify or detect similar or related polynucleotide sequences.

In a one aspect, we disclose nucleotide sequences that can hybridise to a mutant GnT 1 nucleic acid, or a fragment, homologue, variant or derivative thereof, under stringent conditions (e.g. 65° C. and 0.1×SSC {1×SSC=0.15 M NaCl, 0.015 M $Na_3$ Citrate pH 7.0}).

Where a polynucleotide is double-stranded, both strands of the duplex, either individually or in combination, are encompassed by the present disclosure. Where the polynucleotide is single-stranded, it is to be understood that the complementary sequence of that polynucleotide is also disclosed and encompassed.

Polynucleotides which are not 100% homologous to the sequences disclosed here but fall within the disclosure can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of SEQ ID NO: 1 under conditions of medium to high stringency. Similar considerations apply to obtaining species homologues and allelic variants of mutant GnT 1.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, such as at least 20, for example at least 25, 30 or 40 nucleotides in length, and are also encompassed by the term polynucleotides as used herein. Fragments may be less than 500, 200, 100, 50 or 20 nucleotides in length.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15 to 30 nucleotides) flanking a region of the sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

EXAMPLES

Example 1

Cell Culture

Chinese hamster ovary-K1 (CHO-K1) cells are originally obtained from Dr. Donald K. MacCallum (University of Michigan Medical Scholl, Ann Arbor, Mich.).

Parental and mutant CHO cells including JW152 cells are cultured in Dulbecco's Modified Eagle Media (DMEM) supplemented with 10% fetal bovine serum (FBS) at 37° C. in a humidified incubator with 5% $CO_2$.

Lec1.3 cells (Lec 1 cells) are kindly provided by Dr. P. Stanley (Albert Einstein College of Medicine, NY) and cultured in α-MEM (Gibco) supplemented with Proline (40 mg/L) (Invitrogen/Gibco) and 10% FBS.

Example 2

Isolation of RCA-I-Resistant CHO Cells

CHO-K1 cells are cultured in 6-well plates to confluence before culture media is changed to serum-free DMEM. *Ricinus communis* agglutinin I (RCA-I, EY Laboratories) is added into the media to reach a final concentration of 10 μg/ml and incubated with cells overnight.

Then the serum-free DMEM containing RCA-I is replaced with fresh DMEM with 10% FBS. Nine days later, colonies of the CHO cells that survived the RCA-I treatment are picked and cultured in 24 well plates.

These cells are then subjected to agglutination tests using RCA-I to confirm the mutant cells no longer react with RCA-I.

Example 3

Expression Constructs

The coding regions for human erythropoietin (EPO) and several glycosylation related genes are cloned into the pcDNA3.1 vector (Invitrogen).

A DNA fragment that contained the open reading frame of human EPO followed by the internal ribosome entry site (IRES) of the Encephalomyocarditis Virus (EMCV) and the coding region for Chinese hamster N-acetylglucosaminyltransferase I (EPO-IRES-GnT I, or EIG in short) is also cloned into pcDNA3.1. The resulting vector that expresses both EPO and GnT I is called pEIG. To ensure efficient translation, a Kozak consensus sequence (GCCACC) is placed upstream of the translation start codon ATG in each construct.

Example 4

Transient Expression of Recombinant Human EPO in Parental and Mutant CHO Cell Lines Unless specified, 1 μg of DNA construct that expresses EPO and 1 μg of DNA construct that expresses GnT I or another glycosylation related genes are co-transfected into the wild type or JW-152 mutant cells with Lipofectamine (Invitrogen) according to the manufacturer's protocols.

Two days after transfection, conditioned culture media from the transfected cells are collected. The concentrations of recombinant EPO in each transfection sample are determined by standard ELISA using EPO ELISA kits (Roche).

Example 5

Isoelectric Focusing (IEF) Analysis of EPO Produced by Wild Type CHO Cells and JW-152 CHO Cells The sialylation patterns of EPO in different samples are analyzed by IEF followed by Western blot as previously described (Schriebl et al. 2007, Electrophoresis 28:2100-7). The pH range for IEF is 3 to 10.

Example 6

Molecular Cloning and Sequencing Analysis of GnT I cDNA in RCA-I-Resistant CHO Cells For each cell line, $1\times10^7$ cells are pelleted and rinsed in PBS. Total RNA is extracted from the pellet using the RNAqueous kit (Ambion). cDNA is then synthesized through reverse transcription using Moloney Murine Leukemia virus (MMLV) reverse transcriptase (Promega) according to the manufacturer's recommendations The GnT I amplicon from each cell lines' cDNA is obtained through polymerase chain reaction (PCR) using PFX (Invitrogen). This is then cloned into pcDNA 3.1 expression vector and sequenced. A minimum of four clones from each mutant line are sequenced. All plasmid purifications are carried out using mini or midi-preparation kits from Promega. Constructs are sequenced using ABI Prism 3100 Genetic Analyzer (Applied Biosystems) after cycle sequencing with Big Dye 3.1 (Applied Biosystems).

The results are shown at Table D1 above.

Example 7

Isolation of Stably Transfected CHO Cell Lines

CHO-K1 cells are transfected with a construct that expresses EPO alone whilst mutant JW152 cells are transfected with pEIG to express both EPO and GnT I. The transfected cells are selected with G418 (0.8 mg/ml) for two weeks.

Stably transfected cells from the transfected pools are cultured in 96 wells using limiting dilutions. Stable cell lines derived from single transfected cells that expressed EPO are selected using a dot blot analysis and the sialylation patterns of the recombinant EPO expressed by each cell line are analyzed with isoelectric focusing.

Example 8

Results: Isolation and Characterization of RCA-I-Resistant Mutant Cho Cell Lines RCA-I, a plant lectin that is known specific for β-linked galactose residues on glycoproteins or glycolipids, is used to select glycosylation mutants from CHO K1 cells. Most CHO cells are killed by RCA-I after an overnight incubation.

Nine to ten days later cells that survived RCA-I treatment had grown into single clones. These clones are picked and cultured in 24 well plates. One of the clones is named JW152.

To characterize the genetic defect in this cell line, JW152 cells are transfected with a construct to express human EPO. The recombinant EPO produced by JW152 cells is treated with endoglycosidase H (Endo H).

The results are shown in FIG. 1. FIG. 1 shows that JW152 expressed EPO is sensitive to Endo H treatment, suggesting that the glycan structure (N-glycans) found on the EPO molecule are of the high mannose type. It is hence suspected that gene(s) from the early part of the glycosylation pathway is defective.

Based on this observation, a complementation test is carried out. In this test, in addition to the EPO construct, JW152 cells are co-transfected with several genes on the N-glycosylation pathway. These genes include glucosidase I, glucosidase II, mannosidase IA, IB, IC, mannosidase II, GnT I and GnT II. EPO samples produced by JW152 cells in these co-transfection experiments are analyzed by isoelectric focusing (IEF) followed by Western blot.

The results are shown in FIG. 2. The lane on the far left (CHO WT) shows the EPO expressed by the wild type CHO cells as a control. The lane under CHO-JW152 shows the EPO produced by the JW152 cells, showing the incomplete glycosylation of EPO. The rest of the lanes show the EPO produced in JW152 cells that are co-transfected with a different glycosylation related gene as indicated.

Among the genes tested, only GnT I is able to restore the sialylation pattern of EPO produced in JW152 cells. These results suggest that JW152 cells lack functional GnT I gene.

Another important observation made from this IEF/Western blot assay is that in the presence of GnT I, JW152 cells sialylate EPO much better than the wild type cells (comparing with EPO produced by the wild type cells).

To confirm that this difference is due to a unique feature of JW152 cells rather than the result of over expressing GnT I, three CHO cell lines are analyzed by co-transfecting them with a GnT I construct. The recombinant EPO in conditioned media are collected and analyzed by IEF.

Figure 3:
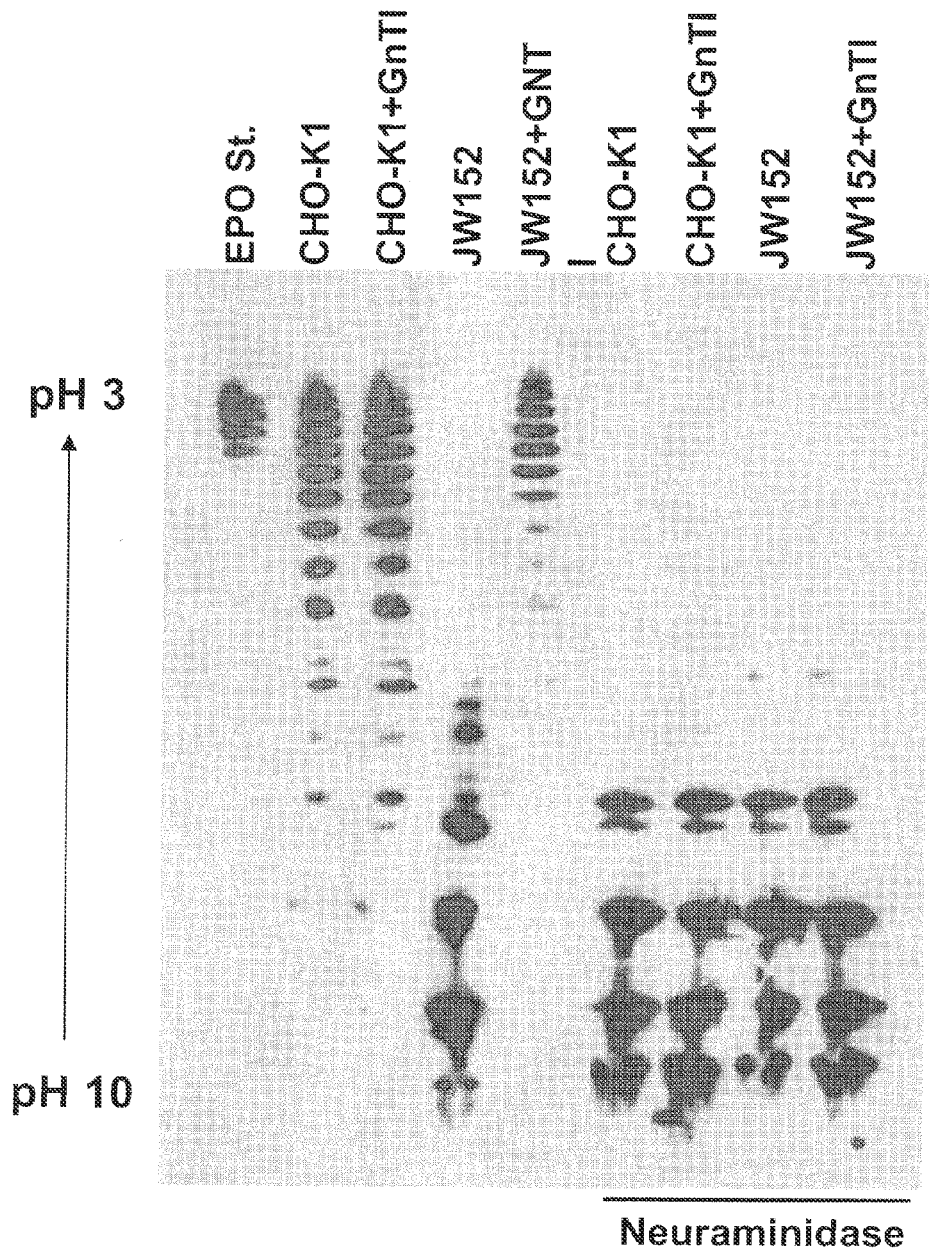
FIG. 3 is a photograph showing that improvement in sialylation after co-transfecting with GnT I is observed for JW152 but not for CHO-K1. The sialylation pattern of EPO produced in CHO-K1, CHO-K1 with co-expression of GnT I. EPO produced in JW152 cells and in JW152 cells with the co-expression of GnT I. The EPO sialylation patterns of CHO-K1 with and without co-expression of GnT I appear to be the same and so, the overexpression of GnT I is not responsible for the betterment in sialylation seen in lane 4. Results suggest that in the presence of GnT I, JW152 cells sialylate recombinant proteins much better than the wild type cells. Treating samples with neuraminidase, which cleaves off sialic acid, results in EPO bands in the acidic region being reduced to the basic region after cleaving off sialic acid, showing that the higher sialylated forms of EPO are indeed focused in the acidic region of the gel.

The results are shown in FIG. 3. GnT I did not improve EPO sialylation in wild CHO cells (comparing lanes CHO-WT and CHO-WT+GnT I). The EPO sialylation patterns of CHO-K1 with and without co-expression of GnT I appear to be the same and so, the overexpression of GnT I is not responsible for the betterment in sialylation seen in the lane labeled CHO-K1 plus GnT1.

GnT I dramatically improved EPO sialylation in JW152 cells (Lane JW152+GnT I). In the presence of GnT I, JW152 cells sialylate EPO much better than wild type CHO cells (comparing lanes CHO-WT and CHO-JW152+GnT I).

FIG. 3 shows that, in the presence of GnT I, JW152 cells sialylate recombinant proteins much better than the wild type cells. Treating samples with neuraminidase, which cleaves off sialic acid result in EPO bands in the acidic region being reduced to the basic region after cleaving off sialic acid, shows that the higher sialylated forms of EPO are indeed focused in the acidic region of the gel.

Lec1 cells are previously isolated by P. Stanley and they are known to lack GnT I activity. The IEF pattern of EPO produced by Lec1 cells (Lec1) is similar to that of EPO produced by JW152. EPO produced by Lec1 cells that are co-transfected with GnT I show a similar sialylation pattern with that produced by the wild type CHO cells.

Figure 4:
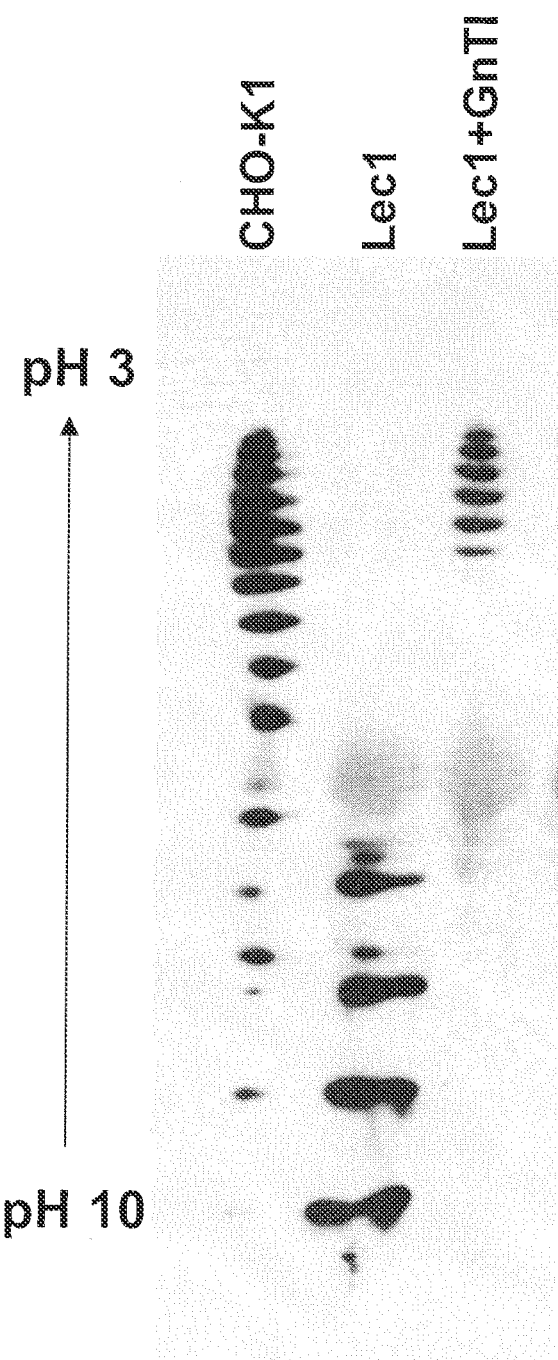
FIG. 4 is a photograph showing that EPO expression in the presence of functional GnT I of previously published Lec 1 mutant which has a GnT I defect is shown to be also highly sialylated. Transient EPO expressed in CHO-K1, Lec 1 and Lec 1 with the restoration of functional GnT I. Lec 1 is previously reported and had been independently isolated using a different lectin by another group headed by Pamela Stanley.

This is shown in FIG. 4. Thus, FIG. 4 shows that EPO expression in the presence of functional GnT I of previously published Lec 1 mutant which has a GnT I defect is also highly sialylated.

Example 9

Results: Stable Expression of Recombinant EPO in JW152 Cells in the Presence of GnT I Data presented in FIG. 2 and FIG. 3 are all from transiently transfected cells. To reveal the sialylation pattern of EPO produced by stably transfected cells, JW152 cells are transfected with pEIG and selected with G418.

After two weeks of selection, single clones are picked and cultured in 24 well plates for two more weeks under the selection pressure of G418. EPO produced by 10 randomly picked such stably transfected clones are analyzed by IEF.

Figure 10:
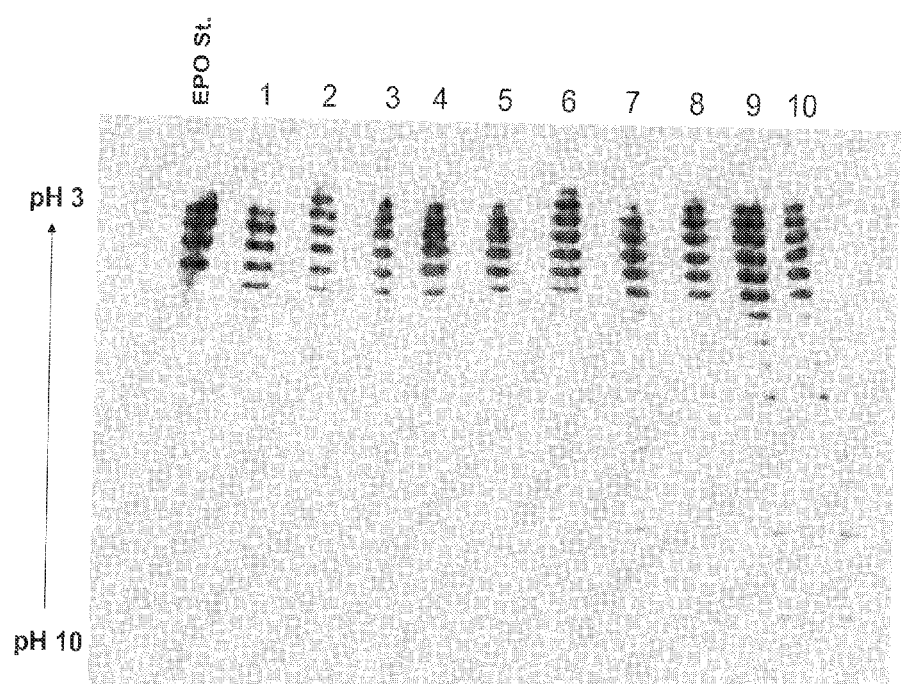
FIG. 10 is a photograph showing that EPO produced in 10 different JW152 clones that are stably transfected with a construct that expresses both EPO and GnT I. JW152 cells are transfected with a construct called pEIG. In pEIG, a transcription unit containing EPO-IRES-GnT I (EIG) is cloned into pcDNA3.1 downstream of the CMV promoter. After transfection, stable clones are selected and picked. The sialylation patterns of EPO produced by 10 such randomly picked clones are analyzed by the IEF/Western blot assay. The results show that all the EPO samples produced by different stable clones are highly sialylated. This means that better sialylation is maintained at stable expression of EPO in the presence of functional GnT I.

As shown in FIG. 10, all the EPO samples produced by different clones are highly sialylated. The sialylation patterns are very similar to that of EPO produced by transiently transfected cells shown in FIG. 3.

Figure 11:
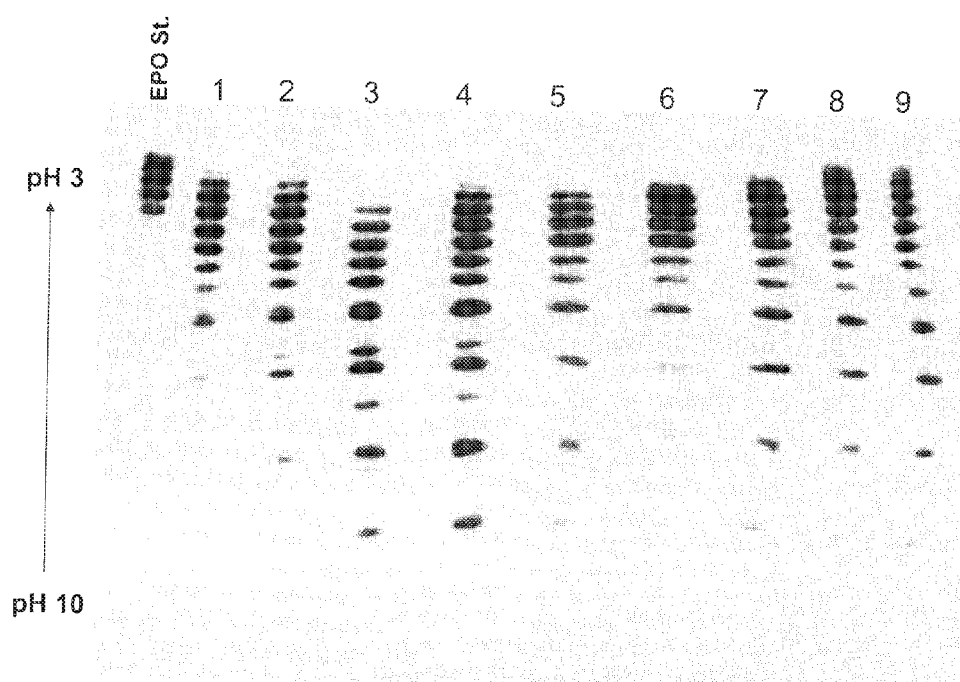
FIG. 11 is a photograph showing that stable expression of EPO in CHO-K1 shows a sialylation profile that is inferior to that of JW152 with restored GnT I function. CHO-K1 cells are transfected with expression vector containing EPO coding sequence and put under selection. Clones are isolated and EPO from nine randomly selected stable clones is analysed with IEF. The results show that all the EPO samples produced by different stable clones vary in overall sialylation but in general are not as well sialylated as those in FIG. 10.

The results shown in FIG. 11 demonstrate that all the EPO samples produced by different stable clones are vary in overall sialylation but in general are not as well sialylated as those in FIG. 10.

Example 10

Results: All the Cho Cells that Survived RCA-I Treatment have Dysfunctional GnT I Gene and they all Sialylate their Proteins Better when Co-Transfected with GnT I RCA-I is known to specifically bind β-Gal residues. Theoretically, as long as the cells do not express β-Gal as the terminal sugar on their surface glycoproteins, they should survive the RCA-I treatment and be isolated as a mutant clones.

We isolated more than 100 mutant CHO clones using RCA-I and hoped that they should carry genetic mutations in different genes. Surprisingly, when the complementation test described in FIG. 2 is carried out, all the clones that survived RCA-I treatment are confirmed to have dysfunctional GnT I genes.

Figure 9:
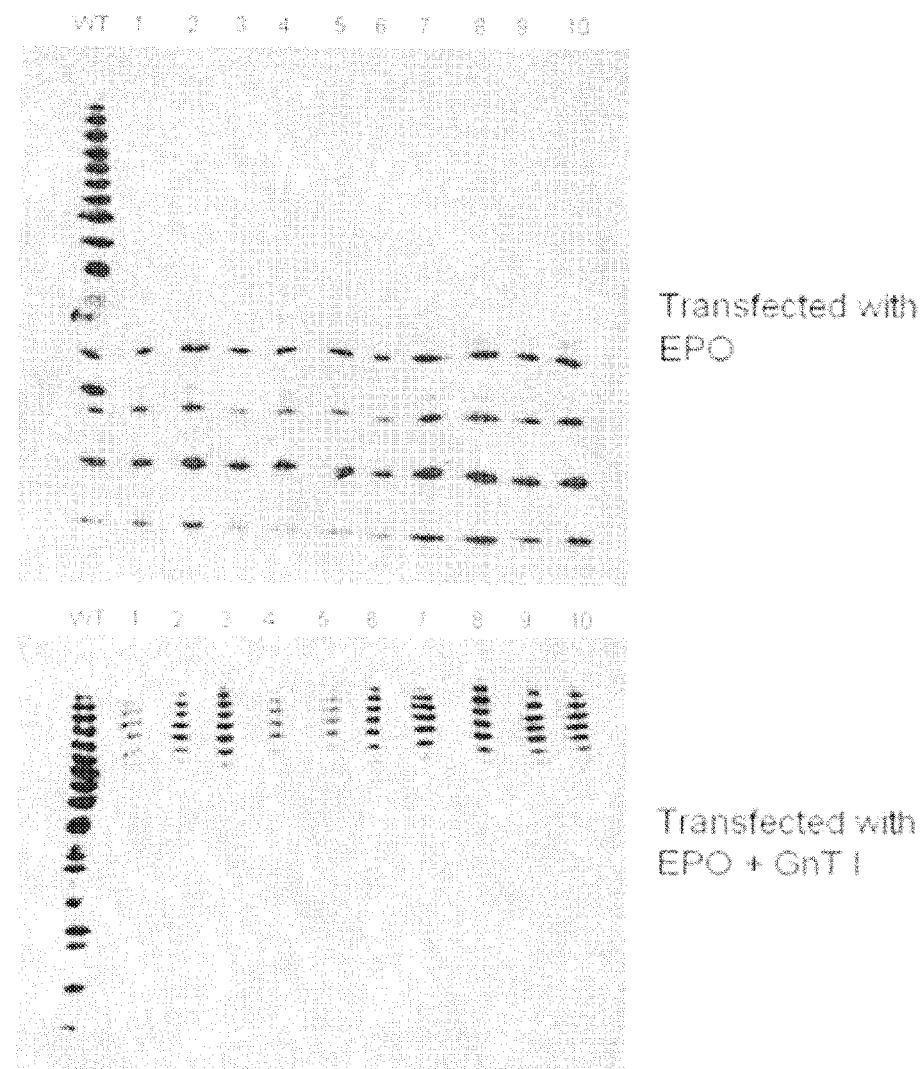
FIG. 9 is a photograph showing recombinant EPO expressed by 10 randomly picked clones isolated by RCA-I. Top gel, EPO expressed in 10 different mutant lines. Cells are transfected with a construct that expresses EPO alone. Bottom gel, EPO expressed in the same set of cell lines that are transfected with pEIG. This construct expresses both EPO and GnT I.

Furthermore, as shown in FIG. 9, EPO produced in these clones are all highly sialylated when co-transfected with GnT I. The mRNA is isolated from some of the mutant lines and reverse transcribed to cDNA. The coding region for GnT I is amplified by PCR using the cDNA as template and cloned into pcDNA3.1.

Sequencing analyses revealed 9 different point mutations in the GnT I gene in these mutant lines, suggesting that they arrived from different original mutant cells (see Table D1 above). Some of them, like JW152, carry a point mutation that results in a premature stop codon. Others carry a mutation that changes an amino acid residue in the GnT I coding region. Nine mutant lines each with a different mutation in the GnT I gene are transfected with pEIG. EPO produced by all nine lines are all highly sialylated when analyzed by IEF (data not shown).

Example 10

Sialylation Patterns in JW152 and Other CHO GnT1 Mutants

Figure 5:
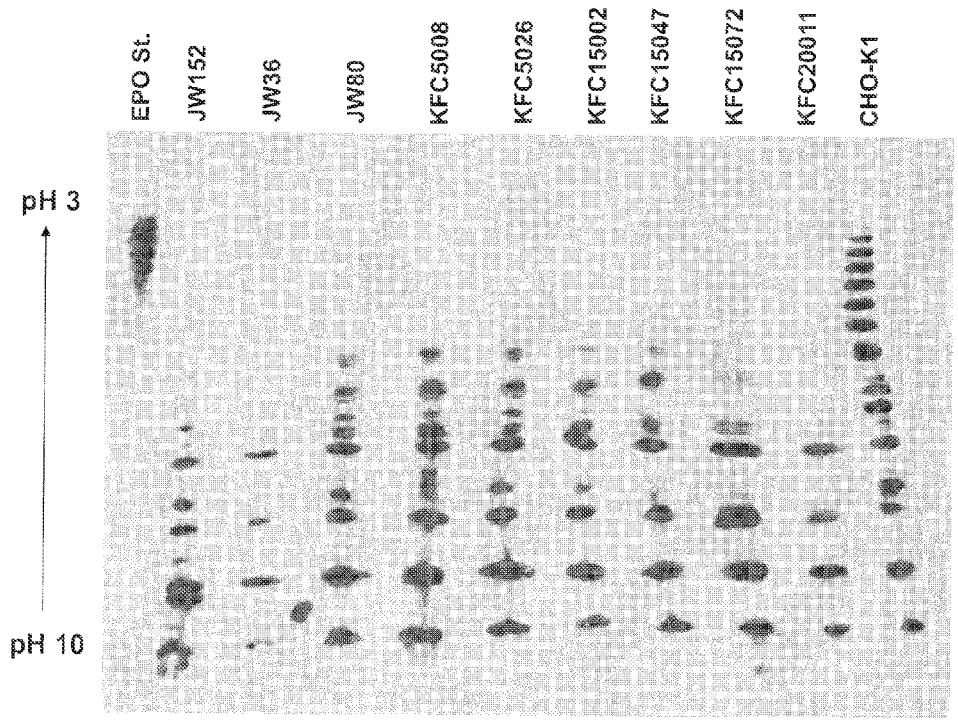
FIG. 5 is a photograph showing that all nine CHO glycosylation mutants, resistant to RCA and bearing distinct mutations in GnT I gene, lead to incomplete sialylation. Transiently expressed EPO in JW152, JW36, JW80, KFC5008, KFC5026, KFC15002, KFC15047, KFC15071, KFC 20011, CHO-K1. EPO produced in nine CHO glycosylation mutants selected with RCA lectin, each bearing a different mutation in the GnT I gene lead to a loss in GnT I function. Incomplete sialylation is observed in these cell lines as compared to CHO wild-type (extreme right). EPO clinical standard is on extreme left. RCA lectin yields mainly GnT I deficient mutants.

As shown in FIG. 5, incomplete sialylation of EPO is observed in nine CHO glycosylation mutants selected with RCA lectin, each bearing a different mutation in the GnT1 gene leading to a loss in GnT1 function, as compared to CHO wild-type.

Figure 6:
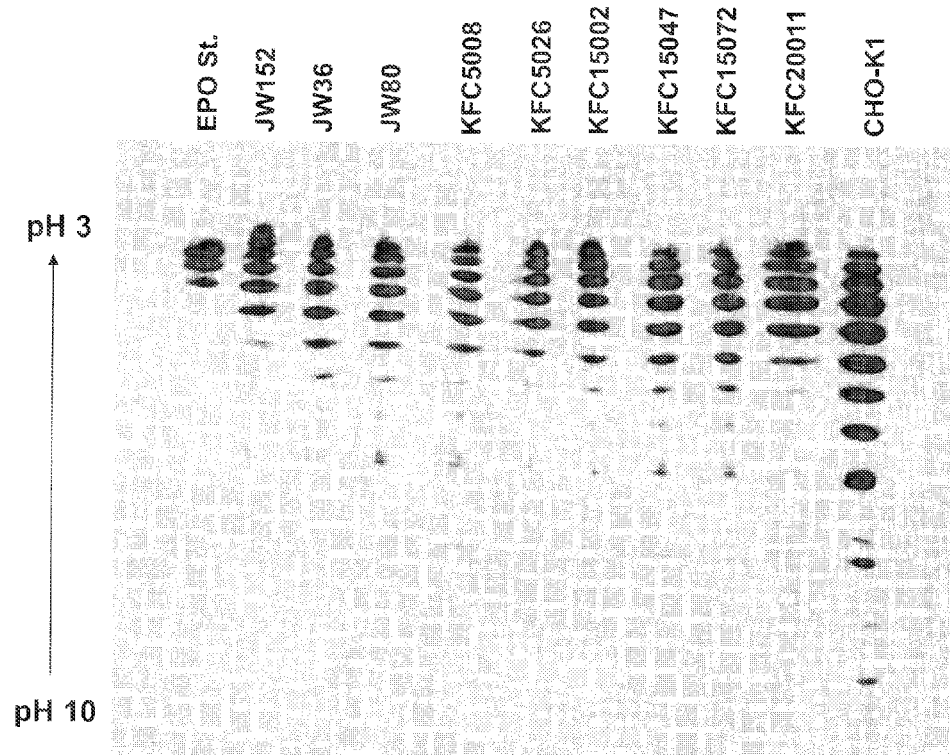
FIG. 6 is a photograph showing that all nine CHO glycosylation mutants, after restoring GnT I function transiently express EPO that is better sialylated than that in CHO-K1.

As shown in FIG. 6, EPO produced in nine CHO glycosylation mutants, each bearing a different mutation in the GnT1 gene, have a sialylation pattern that is superior to CHO wild-type after rescue.

Figure 7:
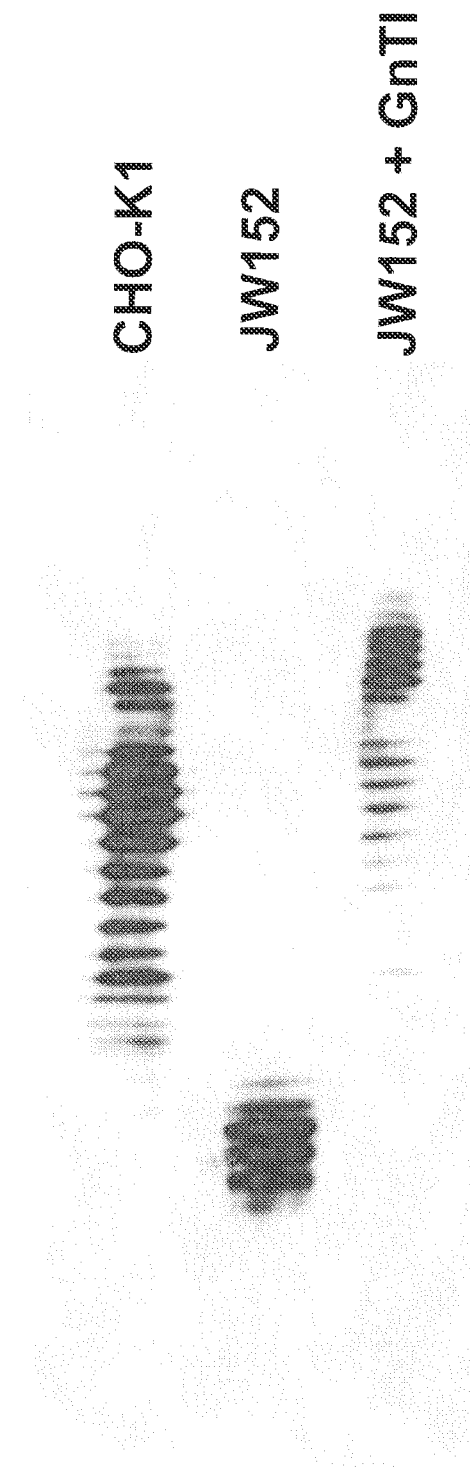
FIG. 7 is a photograph showing that JW152, with restored GnT I function, also sialylates EPO-Fc fusion protein better than CHO-K1. EPO-Fc fusion protein produced in CHO wild-type compared alongside with that produced in JW152 before and after rescue. The results demonstrate that the superior sialylation by rescued JW152 is maintained even with a different model glycoprotein.

FIG. 7 shows the results of an experiment with isoelectric focused samples of a different glycoprotein molecule, EPO-Fc, essentially a erythropoietin fusion protein. The experiment was conducted with a protocol as set out above for EPO expression and IEF analysis, only with an expression vector with a different coding sequence.

The left hand lane shows expression of EPO-Fc in CHO-K1 cells transfected with an expression vector containing EPO-Fc coding sequence. The middle lane shows expression of EPO-Fc in JW152 cells transfected with an expression vector containing EPO-Fc coding sequence. The right hand lane shows expression of EPO-Fc in JW152 cells co-transfected with an expression vector containing EPO-Fc coding sequence and an expression vector containing functional GnT1 coding sequence. As shown in FIG. 7, superior sialylation by rescued JW152 is maintained even with a different model glycoprotein.

The results demonstrate that the superior sialylation by rescued JW152 is maintained even with a different model glycoprotein.

Figure 12:
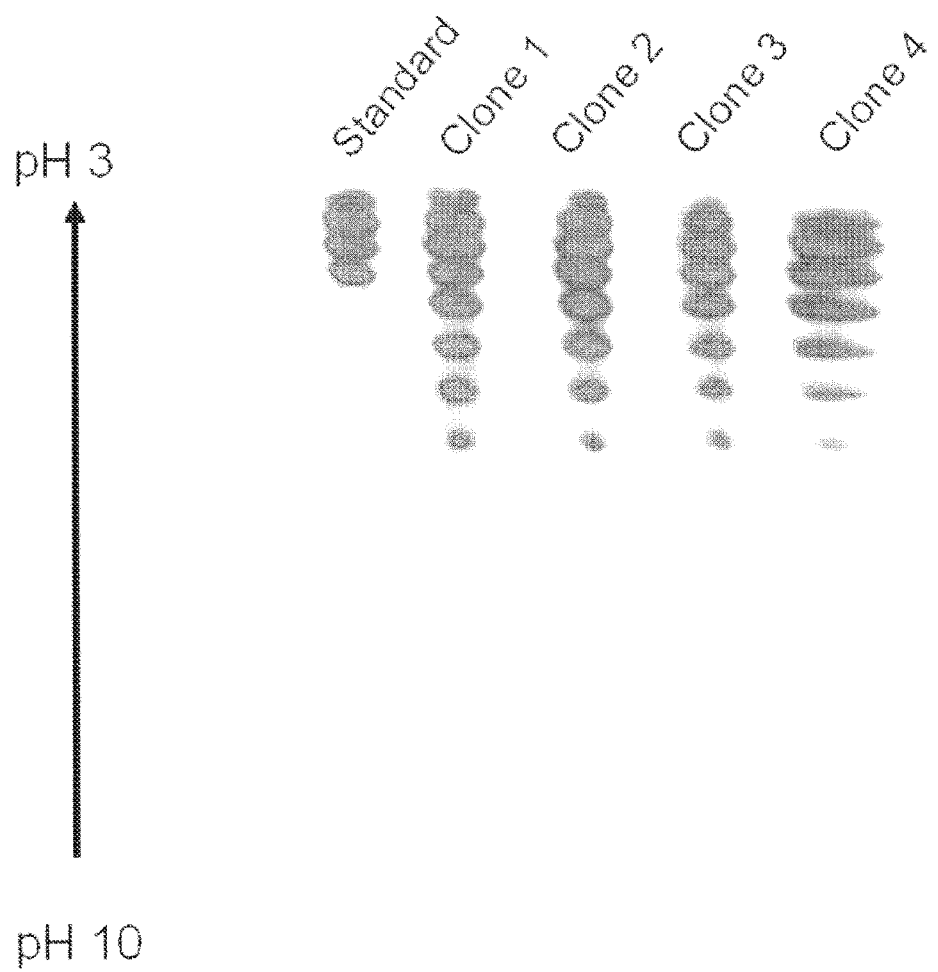
FIG. 12 is a photograph showing that EPO produced in four JW152 stable cell lines that have been adapted to suspension batch culture in protein free medium. The sialylation pattern observed for stable JW152 cell lines in attached culture is maintained in suspension culture.

FIG. 12 shows that the sialylation pattern observed for stable JW152 cell lines in attached culture is maintained in suspension culture.

In conclusion, we have developed a method to isolate novel CHO glycosylation mutant cells. As long as RCA-I is used to treat CHO cells, the surviving cells will have a genetic defect in their GnT I gene. When co-transfected with GnT I, these RCA-I-resistant CHO cells express recombinant glycoproteins with highly sialylated N-glycans.

Example 11

HPAEC Chromatogram

Figure 8:
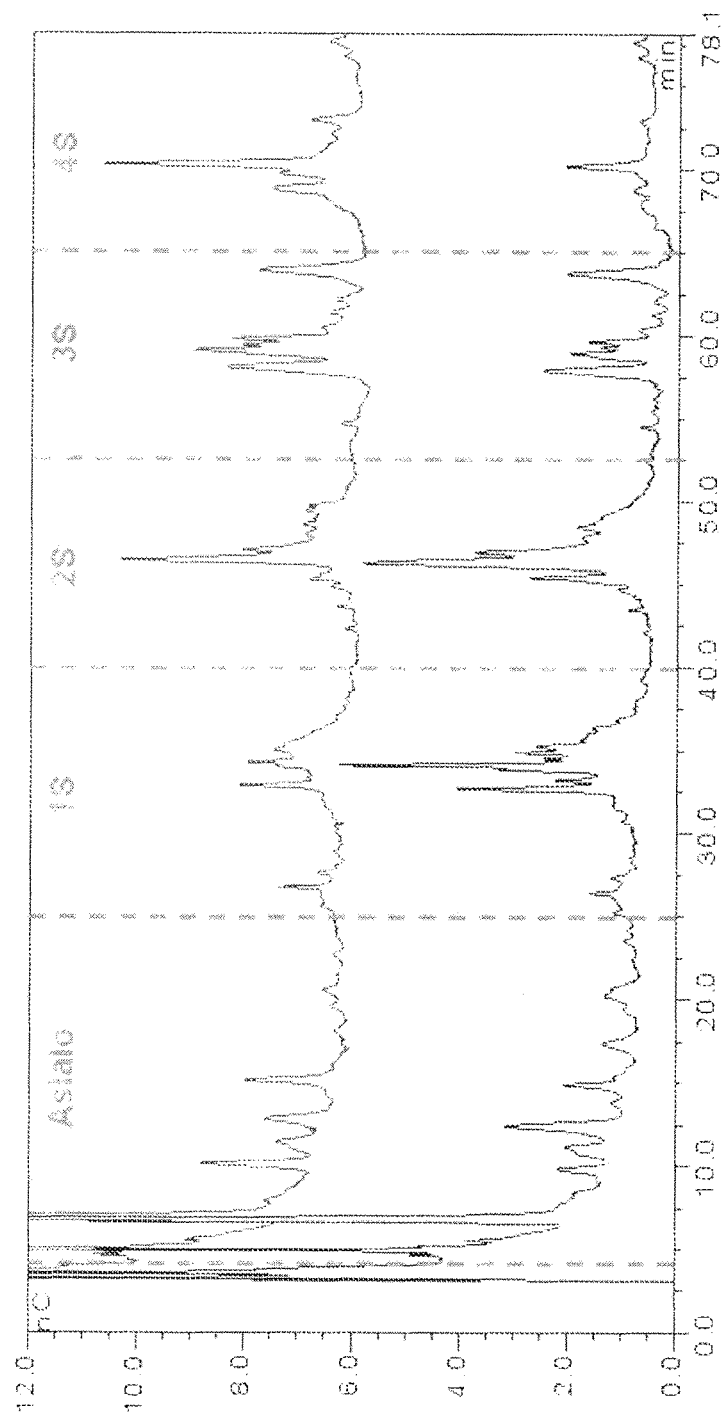
FIG. 8 is a photograph showing that HPAEC chromatogram showing better sialylated glycans cleaved from EPO-Fc expressed in JW152 cells co-expressing functional GnT I. EPO-Fc transiently expressed in CHO-K1 and JW152, con-transfected with GnT I, is purified using affinity purification via a protein A-bound chromatography column. Glycans on the equal amounts of EPO-Fc are cleaved by treatment with Peptide: N-Glycosidase F (PNGase F), and separated, using High pH Anion Exchange Chromatography (HPAEC), according to their number of sialic acids attached to the glycans. The chromatogram shows distinctly higher peaks for the JW152 sample in the 4S group and lower peaks in the 1S group when comparing with the CHO-K1 sample. Arrows point to an internal control, raffinose. Samples are labeled as shown.

FIG. 8 is a photograph showing that HPAEC chromatogram showing better sialylated glycans cleaved from EPO-Fc expressed in JW152 cells co-expressing functional GnT I. EPO-Fc transiently expressed in CHO-K1 and JW152, co-transfected with GnT I, is purified using affinity purification via a protein A-bound chromatography column. Glycans on the equal amounts of EPO-Fc are cleaved by treatment with Peptide: N-Glycosidase F (PNGase F), and separated, using High pH Anion Exchange Chromatography (HPAEC), according to their number of sialic acids attached to the glycans.

The chromatogram shows distinctly higher peaks for the JW152 sample in the 4S group and a lower peak in the 1S group when comparing with the CHO-K1 sample.

REFERENCES

Weikert et al. (1999) Engineering Chinese hamster ovary cells to maximize sialic acid content of recombinant glycoproteins. Nature Biotechnology 17:1116.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A CHO cell comprising a mutation in the GnT I gene selected from the following mutations at the specified position of a GnT I nucleic acid sequence of GenBank Accession Number: AF343963: (a) a C to T transition at nucleic acid sequence position 1015; (b) a G to C transversion at nucleic acid sequence position 1300; (c) an A to C transversion at nucleic acid sequence position 638; (d) a C to G transversion at nucleic acid sequence position 784; (e) a T to A transversion at nucleic acid sequence position 811; (f) an insertion at nucleic acid sequence position 706 resulting in a frame shift from nucleic acid sequence position 236 of the encoded amino acid sequence; (g) a G to A transition at nucleic acid sequence position 246; (h) a G to A transition at nucleic acid sequence position 258; or (i) an A to T transversion at nucleic acid sequence position 859, in which the CHO cell further comprises a nucleic acid encoding a protein of interest comprising a glycoprotein in an expression vector and a nucleic acid encoding a functional GnT I sequence.

2. The CHO cell according to claim 1, in which the protein of interest comprises a glycoprotein, erythropoietin (EPO), interferon-γ (IFN-γ) or Factor VIII.

3. The CHO cell according to claim 1, in which the CHO cell comprises a JW152 cell deposited at ATCC under the Budapest Treaty as accession number PTA-9657.

4. The CHO cell of claim 1, wherein the nucleic acid encoding a protein of interest and the nucleic acid encoding a functional GnT I sequence of GenBank Accession Number AF343963 are comprised by one expression vector.

5. The CHO cell according to claim 4, wherein said expression vector is stably transfected into the CHO cell.

6. The CHO cell according to claim 1, wherein said CHO cell has been adapted to suspension culture or growth in semi-solid medium.

7. A method of providing a CHO cell or cell line comprising a mutation in the GnT I gene (GenBank accession number: AF343963), the method comprising culturing CHO cells in the presence of *Ricinus communis* agglutinin I (RCA-I), in which a recombinant protein of interest expressed by the resulting CHO cell or cell line in the presence of an introduced nucleic acid encoding functional GnT 1 comprises a higher sialylation than a protein of interest expressed by a wild-type Chinese Hamster Ovary cell.

8. The method according to claim 7, in which: (a) the CHO cells are exposed to RCA-I at a concentration of between 0.1 µg/ml to 100 µg/ml; or (b) the CHO cells are exposed RCA-I for a period of from an hour to 3 days.

9. The method according to claim 7, further comprising introducing a nucleic acid encoding a protein of interest and a nucleic acid sequence encoding functional GnT I nucleic acid sequence of GenBank Accession Number AF343963.

10. The method according to claim 7, wherein said nucleic acid encoding a protein of interest and said nucleic acid sequence encoding functional GnT I sequence are comprised in one expression vector.

11. The method according to claim 10, wherein said expression vector is stably transfected into the CHO cell.

12. The method according to claim 7, wherein said cell line been adapted to suspension culture or growth in semi-solid medium.

\* \* \* \* \*